(12) United States Patent
Splinter et al.

(10) Patent No.: US 10,716,625 B2
(45) Date of Patent: *Jul. 21, 2020

(54) LIQUID LIGHT-GUIDE CATHETER WITH OPTICALLY DIVERGING TIP

(71) Applicant: The Spectranetics Corporation, Colorado Springs, CO (US)

(72) Inventors: Robert Splinter, Colorado Springs, CO (US); Robert L. Carver, Colorado Springs, CO (US); Ted A. Giem, Canon City, CO (US); Kevin D. Taylor, Colorado Springs, CO (US); Clint Fix, Grand Junction, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 122 days.

This patent is subject to a terminal disclaimer.

(21) Appl. No.: 15/856,656

(22) Filed: Dec. 28, 2017

(65) Prior Publication Data

US 2018/0116721 A1    May 3, 2018

Related U.S. Application Data

(63) Continuation of application No. 15/243,609, filed on Aug. 22, 2016, now Pat. No. 9,855,100, which is a
(Continued)

(51) Int. Cl.
*A61B 18/20*    (2006.01)
*A61B 18/24*    (2006.01)
(Continued)

(52) U.S. Cl.
CPC .... *A61B 18/24* (2013.01); *A61B 2018/00023* (2013.01); *A61B 2018/00577* (2013.01); *A61B 2018/2261* (2013.01)

(58) Field of Classification Search
None
See application file for complete search history.

(56) References Cited

U.S. PATENT DOCUMENTS 2,667,324 A    1/1954    Hansen
2,828,744 A    4/1958    Mansbach et al.
(Continued)

FOREIGN PATENT DOCUMENTS

EP    0257811 A2    3/1988
EP    0342505 B1    11/1989
(Continued)

OTHER PUBLICATIONS

European Search Report issued in EP Application No. 12815179.2, dated Apr. 28, 2015, 6 pages.
(Continued)

*Primary Examiner* — Lynsey C Eiseman

(57) ABSTRACT

A light-diverting catheter tip is provided according to embodiments disclosed herein. The light-diverting catheter tip may be coupled with the distal tip of a laser catheter and divert at least a portion of the light exiting the distal tip of the laser catheter such that the spot size of the laser beam on an object after exiting the catheter tip is larger than the spot size of the light entering the catheter without the catheter tip. The catheter tip may be removably coupled with the catheter or constructed as part of the catheter. In other embodiment, the catheter tip may conduct fluid and/or divert fluid at the tip of the laser catheter.

11 Claims, 24 Drawing Sheets

Related U.S. Application Data continuation of application No. 12/254,254, filed on Oct. 20, 2008, now Pat. No. 9,421,065, which is a continuation-in-part of application No. 12/176,886, filed on Jul. 21, 2008, now Pat. No. 8,979,828, and a continuation-in-part of application No. 12/061,430, filed on Apr. 2, 2008, now abandoned.

(51) Int. Cl.
 A61B 18/22 (2006.01)
 A61B 18/00 (2006.01)

(56) References Cited

U.S. PATENT DOCUMENTS

| | | | |
|---|---|---|---|
| 2,987,292 A | 6/1961 | Barkell et al. |
| 3,585,996 A | 6/1971 | Pannier et al. |
| 4,013,080 A | 3/1977 | Froning |
| 4,053,845 A | 10/1977 | Gould |
| 4,143,853 A | 3/1979 | Abramson |
| 4,243,034 A | 1/1981 | Brandt |
| 4,264,020 A | 4/1981 | Loiseau |
| 4,274,408 A | 6/1981 | Nimrod |
| 4,333,455 A | 6/1982 | Bodicky |
| 4,417,886 A | 11/1983 | Frankhouser et al. |
| 4,468,224 A | 8/1984 | Enzmann et al. |
| 4,525,157 A | 6/1985 | Vaillancourt |
| 4,540,411 A | 9/1985 | Bodicky |
| 4,564,011 A | 1/1986 | Goldman |
| 4,641,912 A | 2/1987 | Goldenberg |
| 4,655,750 A | 4/1987 | Vaillancourt |
| 4,686,979 A | 8/1987 | Gruen et al. |
| 4,732,448 A | 3/1988 | Goldenberg |
| 4,747,405 A | 5/1988 | Leckrone |
| 4,768,709 A | 9/1988 | Yie |
| 4,784,132 A | 11/1988 | Fox et al. |
| 4,789,104 A | 12/1988 | Anderson |
| 4,799,754 A | 1/1989 | Goldenberg |
| 4,807,620 A | 2/1989 | Strul et al. |
| 4,809,710 A | 3/1989 | Williamson |
| 4,830,460 A | 5/1989 | Goldenberg |
| 4,842,591 A | 6/1989 | Luther |
| 4,844,062 A | 7/1989 | Wells |
| 4,848,336 A | 7/1989 | Fox et al. |
| 4,857,062 A | 8/1989 | Russell |
| 4,860,742 A | 8/1989 | Park et al. |
| 4,863,431 A | 9/1989 | Vaillancourt |
| 4,924,863 A | 5/1990 | Sterzer |
| 4,932,413 A | 6/1990 | Shockey et al. |
| 4,960,411 A | 10/1990 | Buchbinder |
| 4,966,588 A | 10/1990 | Rayman et al. |
| 4,973,329 A | 11/1990 | Park et al. |
| 4,978,341 A | 12/1990 | Niederhauser |
| 5,007,901 A | 4/1991 | Shields |
| 5,011,472 A | 4/1991 | Aebischer et al. |
| 5,011,473 A | 4/1991 | Gatturna |
| 5,016,964 A | 5/1991 | Donnelly |
| 5,041,108 A | 8/1991 | Fox et al. |
| 5,045,065 A | 9/1991 | Raulerson |
| 5,053,013 A | 10/1991 | Ensminger et al. |
| 5,070,882 A | 12/1991 | Bui et al. |
| 5,085,645 A | 2/1992 | Purdy et al. |
| 5,097,841 A | 3/1992 | Moriuchi et al. |
| 5,098,396 A | 3/1992 | Taylor et al. |
| 5,112,328 A | 5/1992 | Taboada et al. |
| 5,116,323 A | 5/1992 | Kreuzer et al. |
| 5,125,903 A | 6/1992 | McLaughlin et al. |
| 5,158,560 A | 10/1992 | Sogawa et al. |
| 5,159,861 A | 11/1992 | Anderson |
| 5,178,153 A | 1/1993 | Einzig |
| 5,179,861 A | 1/1993 | Asano et al. |
| 5,188,632 A | 2/1993 | Goldenberg |
| 5,195,978 A | 3/1993 | Schiffer |
| 5,226,879 A | 7/1993 | Ensminger et al. |
| 5,240,004 A | 8/1993 | Walinsky et al. |
| 5,242,438 A * | 9/1993 | Saadatmanesh ....... A61B 18/24 606/15 |
| 5,246,437 A | 9/1993 | Abela |
| 5,250,045 A | 10/1993 | Bohley |
| 5,250,069 A | 10/1993 | Nobuyoshi et al. |
| 5,263,953 A | 11/1993 | Bagby |
| 5,267,341 A | 11/1993 | Shearin |
| 5,273,042 A | 12/1993 | Lynch et al. |
| 5,281,199 A | 1/1994 | Ensminger et al. |
| 5,295,969 A | 3/1994 | Fischell et al. |
| 5,304,171 A | 4/1994 | Gregory et al. |
| 5,308,318 A | 5/1994 | Plassche et al. |
| 5,325,746 A | 7/1994 | Anderson |
| 5,334,187 A | 8/1994 | Fischell et al. |
| 5,350,375 A | 9/1994 | Deckelbaum et al. |
| 5,352,197 A | 10/1994 | Hammersmark et al. |
| 5,366,441 A | 11/1994 | Crawford |
| 5,395,348 A | 3/1995 | Ryan |
| 5,397,310 A | 3/1995 | Chu et al. |
| 5,415,653 A | 5/1995 | Wardle et al. |
| 5,417,699 A | 5/1995 | Klein et al. |
| 5,429,604 A | 7/1995 | Hammersmark et al. |
| 5,429,617 A | 7/1995 | Hammersmark et al. |
| 5,440,664 A | 8/1995 | Harrington et al. |
| 5,454,782 A | 10/1995 | Perkins |
| 5,456,284 A | 10/1995 | Ryan et al. |
| 5,456,680 A | 10/1995 | Taylor et al. |
| 5,468,239 A | 11/1995 | Tanner et al. |
| 5,470,330 A | 11/1995 | Goldenberg et al. |
| 5,484,433 A | 1/1996 | Taylor et al. |
| 5,489,274 A | 2/1996 | Chu et al. |
| 5,497,782 A | 3/1996 | Fugoso |
| 5,501,227 A | 3/1996 | Yock |
| 5,501,671 A | 3/1996 | Rosen et al. |
| 5,514,128 A | 5/1996 | Hillsman et al. |
| 5,520,665 A | 5/1996 | Fleetwood |
| 5,537,499 A | 7/1996 | Brekke |
| 5,540,236 A | 7/1996 | Ginn |
| 5,571,151 A | 11/1996 | Gregory |
| 5,573,516 A | 11/1996 | Tyner |
| 5,573,531 A | 11/1996 | Gregory |
| 5,607,419 A | 3/1997 | Amplatz et al. |
| 5,613,663 A | 3/1997 | Schmidt et al. |
| 5,623,940 A | 4/1997 | Daikuzono |
| 5,643,251 A | 7/1997 | Hillsman et al. |
| 5,649,923 A | 7/1997 | Gregory et al. |
| 5,685,862 A | 11/1997 | Mahurkar |
| 5,702,367 A | 12/1997 | Cover et al. |
| 5,704,914 A | 1/1998 | Stocking et al. |
| 5,722,972 A | 3/1998 | Power et al. |
| 5,749,861 A | 5/1998 | Guala et al. |
| 5,769,843 A | 6/1998 | Abela et al. |
| 5,817,144 A | 10/1998 | Gregory |
| 5,820,596 A | 10/1998 | Rosen et al. |
| 5,824,026 A | 10/1998 | Diaz |
| 5,827,234 A | 10/1998 | Loos et al. |
| 5,836,946 A | 11/1998 | Diaz et al. |
| 5,843,046 A | 12/1998 | Motisi et al. |
| RE36,104 E | 2/1999 | Solar |
| 5,865,801 A | 2/1999 | Houser |
| 5,879,338 A | 3/1999 | Mahurkar |
| 5,921,970 A | 7/1999 | Vandenberg |
| 5,968,036 A | 10/1999 | Goodman et al. |
| 5,976,124 A | 11/1999 | Reiser |
| 5,980,492 A | 11/1999 | Rosen et al. |
| 5,989,223 A | 11/1999 | Chu et al. |
| 5,989,243 A | 11/1999 | Goldenberg |
| 5,989,700 A | 11/1999 | Krivopal |
| 5,993,443 A | 11/1999 | Murphy-Chutorian et al. |
| 6,007,522 A | 12/1999 | Agro et al. |
| 6,022,342 A | 2/2000 | Mukherjee |
| 6,039,726 A | 3/2000 | Lewis et al. |
| 6,066,130 A | 5/2000 | Gregory et al. |
| 6,096,009 A | 8/2000 | Windheuser et al. |
| 6,117,128 A | 9/2000 | Gregory |
| 6,152,910 A | 11/2000 | Agro et al. |
| 6,156,029 A | 12/2000 | Mueller |
| 6,163,641 A | 12/2000 | Eastgate |
| 6,165,215 A | 12/2000 | Rottenberg et al. |

(56) References Cited

U.S. PATENT DOCUMENTS

| | | |
|---|---|---|
| 6,176,852 B1 | 1/2001 | Ischinger |
| 6,196,230 B1 | 3/2001 | Hall et al. |
| 6,197,001 B1 | 3/2001 | Wilson et al. |
| 6,235,001 B1 | 5/2001 | O'Holloran et al. |
| 6,271,621 B1 | 8/2001 | Ito et al. |
| 6,287,280 B1 | 9/2001 | Lampropoulos et al. |
| 6,290,668 B1 | 9/2001 | Gregory et al. |
| 6,290,710 B1 | 9/2001 | Cryer et al. |
| 6,312,404 B1 | 11/2001 | Agro et al. |
| 6,315,753 B1 | 11/2001 | Cragg et al. |
| 6,346,093 B1 | 2/2002 | Allman et al. |
| 6,458,098 B1 | 10/2002 | Kanesaka |
| 6,488,667 B1 | 12/2002 | Murphy |
| 6,488,674 B2 | 12/2002 | Becker et al. |
| 6,491,647 B1 | 12/2002 | Bridger et al. |
| 6,520,951 B1 | 2/2003 | Carrillo et al. |
| 6,551,302 B1 | 4/2003 | Rosinko et al. |
| 6,572,590 B1 | 6/2003 | Stevens et al. |
| 6,572,791 B2 | 6/2003 | Sakata et al. |
| 6,582,401 B1 | 6/2003 | Windheuser et al. |
| 6,606,515 B1 | 8/2003 | Windheuser et al. |
| 6,663,597 B1 | 12/2003 | Windheuser et al. |
| 6,694,983 B2 | 2/2004 | Wolf et al. |
| 6,743,208 B1 | 6/2004 | Coyle |
| 6,746,442 B2 | 6/2004 | Agro et al. |
| 6,763,722 B2 | 7/2004 | Fjield et al. |
| 6,808,498 B2 | 10/2004 | Laroya et al. |
| 6,869,416 B2 | 3/2005 | Windheuser et al. |
| 6,879,854 B2 | 4/2005 | Windheuser et al. |
| 6,886,411 B2 | 5/2005 | Kjellman et al. |
| 6,963,688 B2 | 11/2005 | Nath |
| 6,974,422 B1 | 12/2005 | Millar |
| 6,994,695 B1 | 2/2006 | Millar |
| 6,997,908 B2 | 2/2006 | Carrillo et al. |
| 7,008,404 B2 | 3/2006 | Nakajima |
| 7,025,746 B2 | 4/2006 | Tal |
| 7,060,052 B2 | 6/2006 | Windheuser et al. |
| 7,076,285 B2 | 7/2006 | Windheuser et al. |
| 7,172,577 B2 | 2/2007 | Mangano et al. |
| 7,179,252 B2 | 2/2007 | Agro et al. |
| 7,241,285 B1 | 7/2007 | Dikeman |
| 7,261,703 B2 | 8/2007 | Lampropoulos et al. |
| 7,355,182 B2 | 4/2008 | Szu |
| 7,396,343 B2 | 7/2008 | Brown |
| 7,544,184 B2 | 6/2009 | Cope et al. |
| 7,544,193 B2 | 6/2009 | Agro et al. |
| 7,578,814 B2 | 8/2009 | Accisano et al. |
| 7,615,033 B2 | 11/2009 | Leong |
| 7,678,129 B1 | 3/2010 | Gesswein et al. |
| 7,682,340 B2 | 3/2010 | Funamura et al. |
| 7,706,861 B2 | 4/2010 | Windheuser et al. |
| 7,708,721 B2 | 5/2010 | Khaw |
| 7,722,567 B2 | 5/2010 | Tal |
| 7,760,316 B2 | 7/2010 | Hirakata et al. |
| 7,766,049 B2 | 8/2010 | Miller et al. |
| 7,819,844 B2 | 10/2010 | Spenser et al. |
| 7,846,133 B2 | 12/2010 | Windheuser et al. |
| 7,909,811 B2 | 3/2011 | Agro et al. |
| 7,918,859 B2 | 4/2011 | Katoh et al. |
| 8,006,953 B2 | 8/2011 | Bennett |
| 8,043,208 B2 | 10/2011 | Windheuser et al. |
| 8,052,647 B2 | 11/2011 | Raulerson et al. |
| 8,066,669 B2 | 11/2011 | Christensen et al. |
| 8,066,670 B2 | 11/2011 | Cluff et al. |
| 8,066,679 B2 | 11/2011 | Hwang |
| 8,083,690 B2 | 12/2011 | Peterson et al. |
| 8,105,286 B2 | 1/2012 | Anderson et al. |
| 8,128,598 B2 | 3/2012 | Uihlein |
| 8,177,760 B2 | 5/2012 | Rome et al. |
| 8,202,251 B2 | 6/2012 | Bierman et al. |
| 8,202,254 B2 | 6/2012 | Schweikert et al. |
| 8,206,283 B2 | 6/2012 | Windheuser et al. |
| 8,206,375 B2 | 6/2012 | Snow |
| 8,211,087 B2 | 7/2012 | Carter et al. |
| 8,216,295 B2 | 7/2012 | Benjamin et al. |
| 8,257,382 B2 | 9/2012 | Rottenberg et al. |
| 8,257,383 B2 | 9/2012 | Rottenberg et al. |
| 8,979,828 B2 | 3/2015 | Fix |
| 9,066,742 B2 | 6/2015 | Splinter |
| 9,162,038 B2 | 10/2015 | Rottenberg et al. |
| 9,289,173 B2 | 3/2016 | Splinter |
| 9,339,337 B2 | 5/2016 | Fix |
| 9,421,065 B2 | 8/2016 | Splinter et al. |
| 9,855,100 B2 | 1/2018 | Splinter et al. |
| 2001/0003790 A1 | 6/2001 | Ben-Haim et al. |
| 2001/0034501 A1 | 10/2001 | Tom |
| 2002/0026188 A1 | 2/2002 | Balbierz et al. |
| 2002/0068885 A1 | 6/2002 | Harhen et al. |
| 2002/0072647 A1 | 6/2002 | Schock et al. |
| 2002/0188313 A1 | 12/2002 | Johnson et al. |
| 2003/0051733 A1 | 3/2003 | Kotmel et al. |
| 2003/0216685 A1 | 11/2003 | Porter |
| 2004/0060362 A1 | 4/2004 | Kjellmann et al. |
| 2004/0079429 A1 | 4/2004 | Miller et al. |
| 2004/0131299 A1 | 7/2004 | Adoram et al. |
| 2004/0199156 A1 | 10/2004 | Rioux et al. |
| 2004/0215146 A1 | 10/2004 | Lampropoulos et al. |
| 2005/0131289 A1 | 6/2005 | Aharoni et al. |
| 2005/0143770 A1 | 6/2005 | Carter et al. |
| 2005/0148925 A1 | 7/2005 | Rottenberg et al. |
| 2005/0159770 A1 | 7/2005 | Divani et al. |
| 2005/0192637 A1 | 9/2005 | Girouard et al. |
| 2005/0251116 A1 | 11/2005 | Steinke et al. |
| 2006/0013533 A1 | 1/2006 | Slatkine |
| 2006/0020241 A1 | 1/2006 | Piskun et al. |
| 2006/0079813 A1 | 4/2006 | Schlumpf |
| 2006/0235314 A1 | 10/2006 | Migliuolo et al. |
| 2006/0264834 A1 | 11/2006 | Vaillancourt |
| 2007/0118079 A1 | 5/2007 | Moberg et al. |
| 2007/0162071 A1 | 7/2007 | Burkett et al. |
| 2007/0233185 A1 | 10/2007 | Anderson et al. |
| 2007/0270931 A1 | 11/2007 | Leanna et al. |
| 2008/0159825 A1 | 7/2008 | Tegg |
| 2008/0161794 A1 | 7/2008 | Wang et al. |
| 2008/0234567 A1 | 9/2008 | Tearney et al. |
| 2008/0243065 A1 | 10/2008 | Rottenberg et al. |
| 2008/0243067 A1 | 10/2008 | Rottenberg et al. |
| 2008/0300574 A1 | 12/2008 | Belson et al. |
| 2008/0300662 A1 | 12/2008 | Taylor |
| 2008/0306499 A1 | 12/2008 | Katoh et al. |
| 2009/0005754 A1 | 1/2009 | Soetermans |
| 2009/0221961 A1 | 9/2009 | Tal et al. |
| 2009/0254074 A1 | 10/2009 | Splinter et al. |
| 2009/0292253 A1 | 11/2009 | Raulerson et al. |
| 2010/0016842 A1 | 1/2010 | Fix |
| 2010/0094310 A1 | 4/2010 | Warring et al. |
| 2010/0137892 A1 | 6/2010 | Krolik et al. |
| 2011/0021994 A1 | 1/2011 | Anderson et al. |
| 2011/0060315 A1 | 3/2011 | Windheuser et al. |
| 2011/0077621 A1 | 3/2011 | Graham et al. |
| 2011/0144572 A1 | 6/2011 | Kassab et al. |
| 2011/0196344 A1 | 8/2011 | Agro et al. |
| 2011/0251559 A1 | 10/2011 | Tal et al. |
| 2011/0270192 A1 | 11/2011 | Anderson et al. |
| 2011/0276002 A1 | 11/2011 | Bierman |
| 2011/0282285 A1 | 11/2011 | Blanchard et al. |
| 2012/0041371 A1 | 2/2012 | Tal et al. |
| 2012/0184896 A1 | 7/2012 | DeLegge et al. |
| 2012/0220942 A1 | 8/2012 | Hall et al. |
| 2012/0265229 A1 | 10/2012 | Rottenberg et al. |
| 2012/0265233 A1 | 10/2012 | Waisman et al. |
| 2013/0165867 A1 | 6/2013 | Isaacson et al. |
| 2015/0148790 A1 | 5/2015 | Fix |
| 2015/0245796 A1 | 9/2015 | Splinter |
| 2016/0000454 A1 | 1/2016 | Rottenberg et al. |
| 2016/0183844 A1 | 6/2016 | Splinter |
| 2016/0310214 A1 | 10/2016 | Fix |

FOREIGN PATENT DOCUMENTS

| | | |
|---|---|---|
| EP | 0388112 B1 | 9/1990 |
| EP | 0623673 A2 | 11/1994 |
| EP | 0633184 A1 | 1/1995 |
| EP | 0650666 A1 | 5/1995 |

(56) References Cited

FOREIGN PATENT DOCUMENTS

| | | |
|---|---|---|
| EP | 0724098 A1 | 7/1996 |
| EP | 0846064 A1 | 6/1998 |
| EP | 0897295 A1 | 2/1999 |
| EP | 1035880 A1 | 9/2000 |
| EP | 1045708 A1 | 10/2000 |
| EP | 1098671 A1 | 5/2001 |
| EP | 1109590 A1 | 6/2001 |
| EP | 1399549 A1 | 3/2004 |
| EP | 1441672 A1 | 8/2004 |
| EP | 1546664 A1 | 6/2005 |
| EP | 1771132 A2 | 4/2007 |
| EP | 1789122 A2 | 5/2007 |
| EP | 2055266 A2 | 5/2009 |
| EP | 2012660 B1 | 9/2009 |
| EP | 2131913 A1 | 12/2009 |
| EP | 2163216 A2 | 3/2010 |
| EP | 2163217 A2 | 3/2010 |
| EP | 2185107 A1 | 5/2010 |
| EP | 2470248 | 3/2011 |
| EP | 2399550 A1 | 12/2011 |
| EP | 2473123 A1 | 7/2012 |
| EP | 2494419 A2 | 9/2012 |
| EP | 2512577 A2 | 10/2012 |
| EP | 1796597 B1 | 1/2013 |
| WO | WO198809188 A | 12/1988 |
| WO | WO199306878 A | 4/1993 |
| WO | WO199706973 A | 2/1997 |
| WO | WO199828034 A | 7/1998 |

OTHER PUBLICATIONS

Ghosh, Sharmila. "Experimental Investigation of Surface Plasmon Resonance Using Tapered Cylindrical Light Guides With Metal-Dielectric Interface." Journal of Sensor Technology, 2:48-54, 2012.

Grundfest, Warren S., MD, et al., "Laser Ablation of Human Atherosclerotic Plaque Without Adjacent Tissue Injury," JACC vol. 5, No. 4, (Apr. 1985), pp. 929-933.

International Search Report and Written Opinion issued in PCT/US2008/082732 dated Dec. 29, 2008, 6 pages.

Merit Medical Systems, Inc. Merit Marquis Flow Switch: Traditional Premarket Notification 510(k). Section 510(k) summary, Jul. 1, 2011, 6 pages.

MeritMedical Flow Control Switch—Instructions for Use. Merit Medical Systems, Inc. 2 pages. This document and/or corresponding part was potentially available prior to the filing date of the present application and/or the relevant priority date(s) of the present application.

MeritMedical: Flow Control Switch Confidently Control Fluid Flow. Merit Medical Systems, Inc. 2 pages. This document and/or corresponding part was potentially available prior to the filed of the present application and/or the relevant priority date(s) of the present application.

NAMIC® Fluid Management: Constructed for Confidence. Configured for Care. Systems for Cardiac Catheterization Labs. Navilyst Medical, Inc. 2009, 11 pages.

Office Action for U.S. Appl. No. 12/061,430 dated Dec. 19, 2008, 10 pages.

Office Action for U.S. Appl. No. 12/176,886 dated Jan. 25, 2013, 10 pages.

Office Action for U.S. Appl. No. 12/176,886 dated Sep. 26, 2012, 12 pages.

Product Catalogue: Peripheral Interventions Vascular Surgery, Boston Scientific, 147 pages, 2007.

Qosina Part No. 97337 (Inline Flow Control Switch). Dec. 1, 2012, 1 page.

U.S. Appl. No. 12/254,254, filed Oct. 20, 2008 entitled Liquid Light-Guide Catheter With Optically Diverging TIP.

U.S. Appl. No. 12/061,430, filed Apr. 2, 2008 entitled Laser With Tapered Waveguide.

Wilburn, Susan O. "Needlestick and Sharps Injury Prevention." Online Journal of Issues in Nursing, 9(3), [Abstract]. Retreived Sep. 5, 2017 from the Internet: http:/www.nursingworld.org/MainMenuCategories/ANAMarketplace/ANAPeriodicals/OJIN/TableofContentsVolume92004/No3Sept04/InjuryPrevention.html.

U.S. Appl. No. 15/243,609, filed Aug. 22, 2016 entitled Liquid Light-Guide Catheter With Optically Diverging TIP.

* cited by examiner

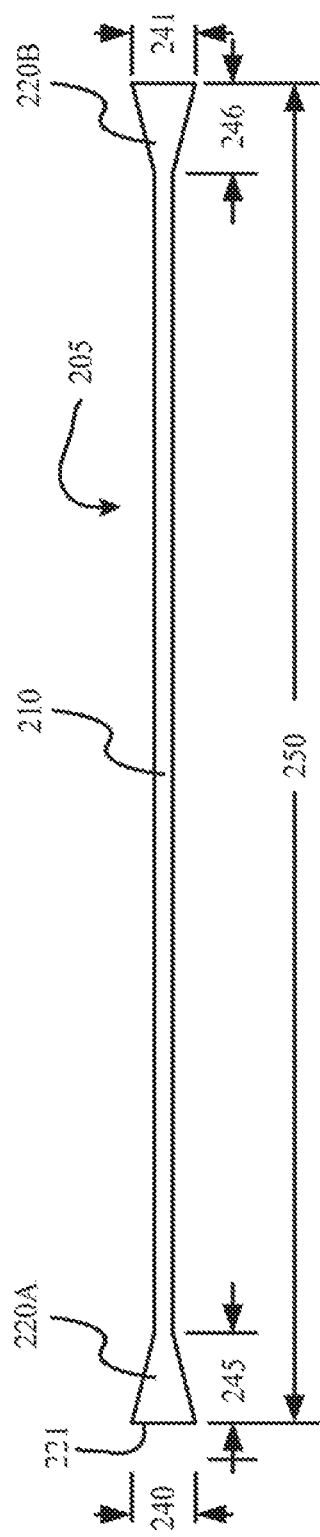
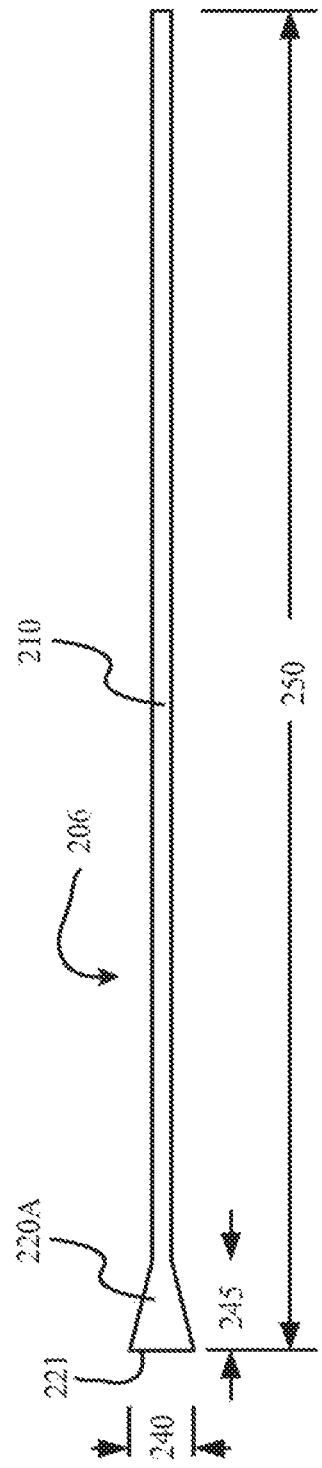
FIG 2A
FIG 2B

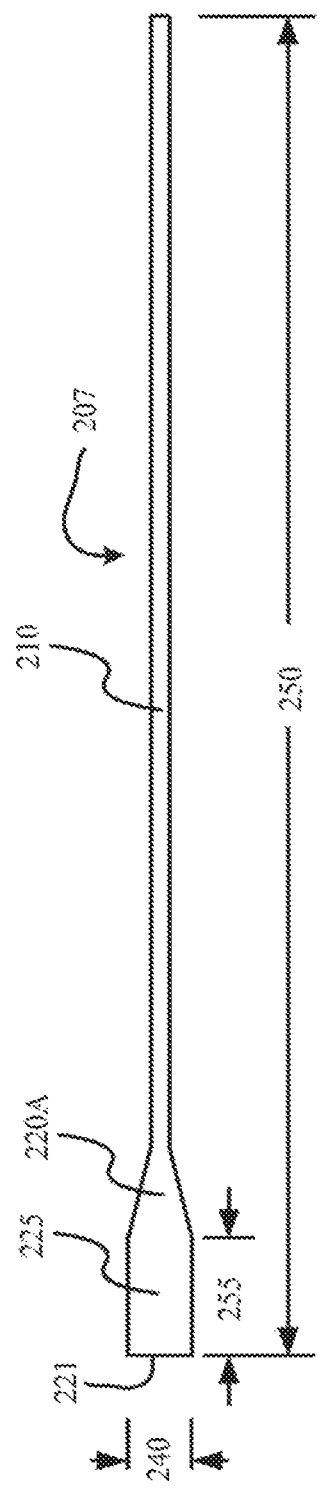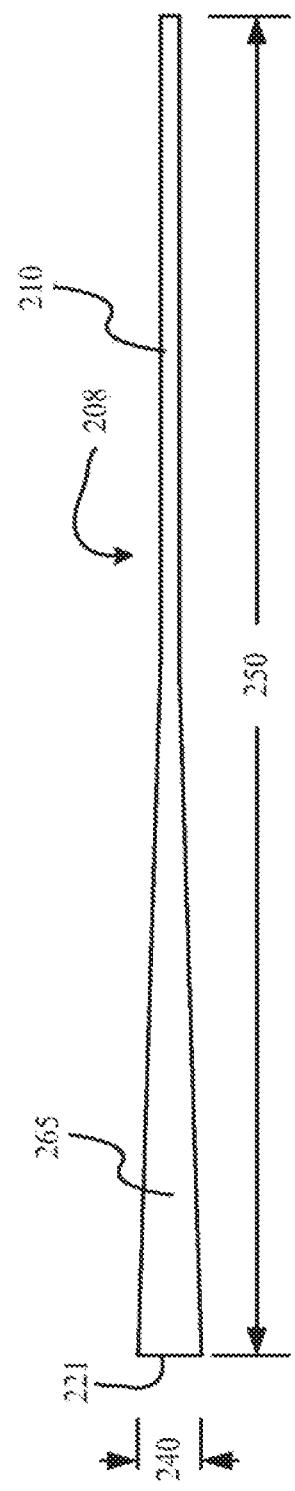

SECTION A-A

SECTION B-B

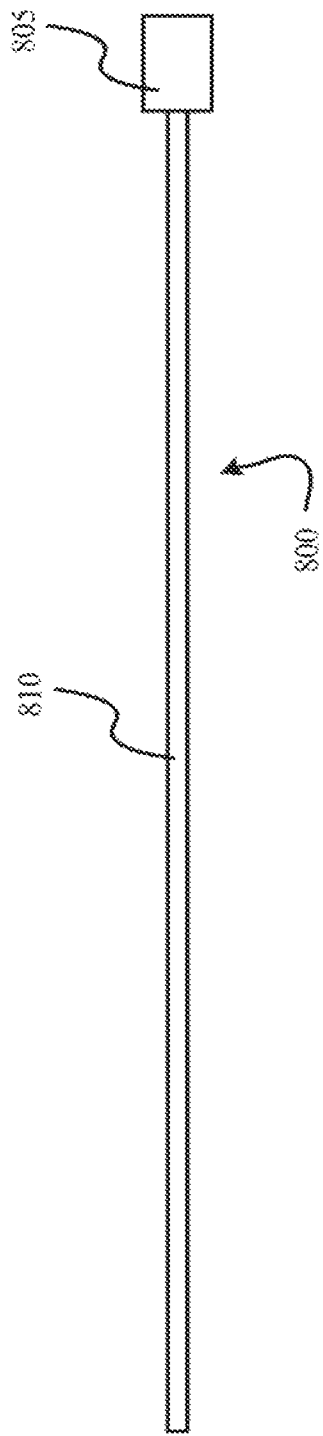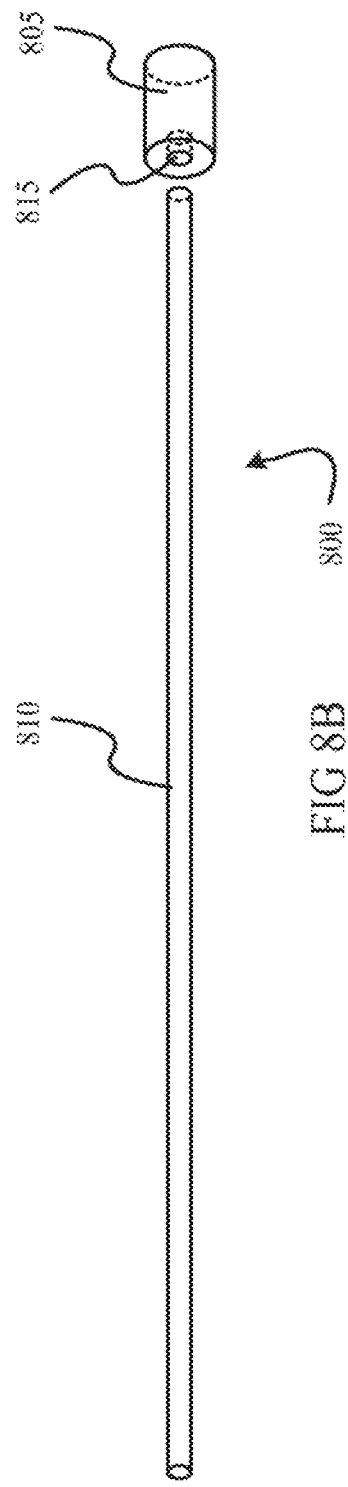
FIG 8A
FIG 8B

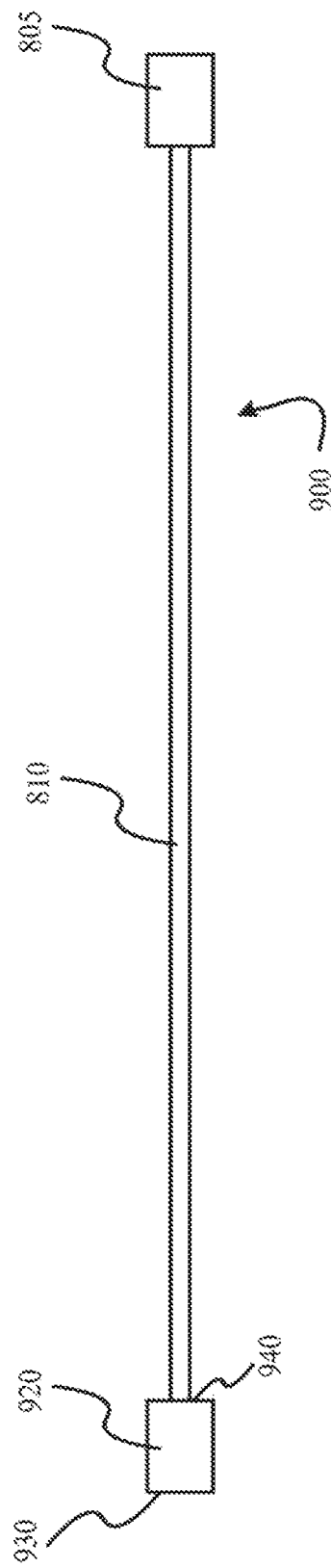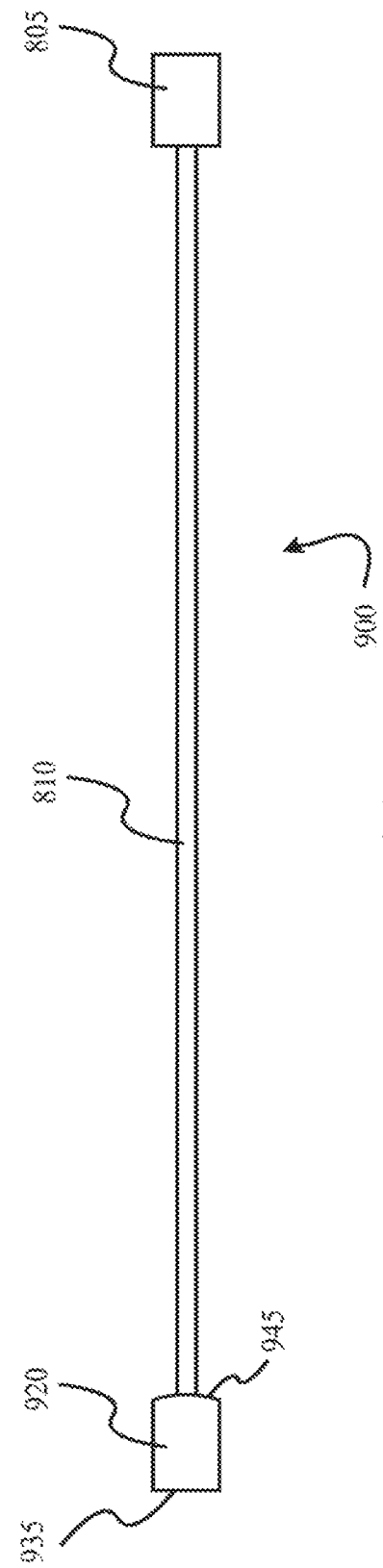

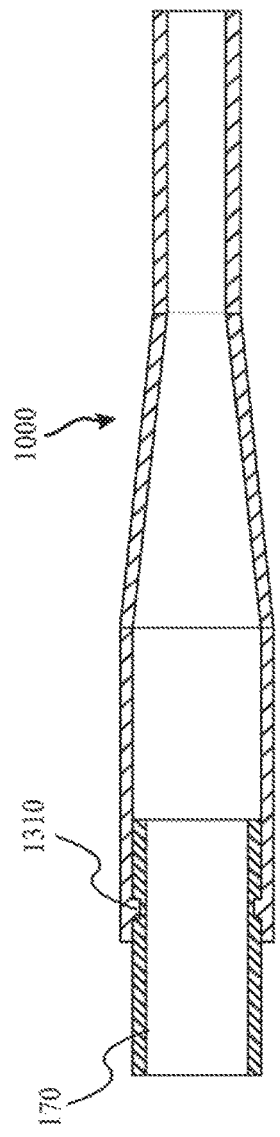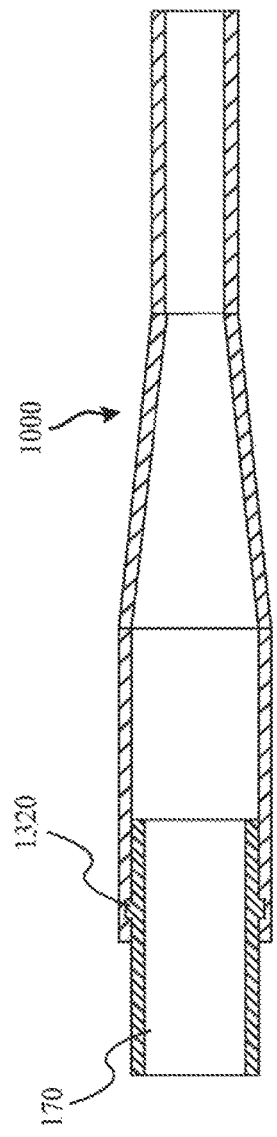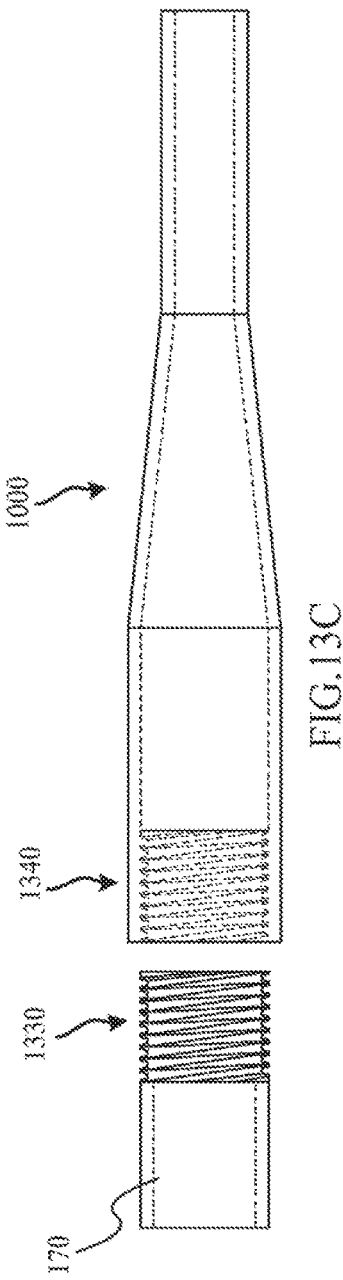

LIQUID LIGHT-GUIDE CATHETER WITH OPTICALLY DIVERGING TIP

CROSS-REFERENCES TO RELATED APPLICATIONS

The present application is a continuation of U.S. patent application Ser. No. 15/243,609, filed Aug. 22, 2016, entitled "LIQUID LIGHT-GUIDE CATHETER WITH OPTICALLY DIVERGING TIP," now U.S. Pat. No. 9,855, 100, issued on Jan. 2, 2018, which is a continuation of U.S. patent application Ser. No. 12/254,254, filed Oct. 20, 2008, entitled "LIQUID LIGHT-GUIDE CATHETER WITH OPTICALLY DIVERGING TIP," now U.S. Pat. No. 9,421, 065, issued on Aug. 23, 2016, which is a continuation-in-part of commonly assigned U.S. patent application Ser. No. 12/176,886, filed Jul. 21, 2008, entitled "Tapered Liquid Light Guide," now U.S. Pat. No. 8,979,828, issued on Mar. 17, 2015, and U.S. patent application Ser. No. 12/061,430, filed Apr. 2, 2008, entitled "Laserwire With Tapered Waveguide," now abandoned, the entirety of each of which is herein incorporated by reference for all purposes.

BACKGROUND OF THE INVENTION

This disclosure relates in general to light guides and, but not by way of limitation, to liquid light guides and/or catheters with diverging or converging tips among other things.

Catheters containing optical fibers transmit energy to irradiate internal parts of the body for diagnostic and therapeutic purposes. There are many medical applications in which it is desirable to deliver energy, such as laser energy, through an optical fiber or similar waveguide device disposed in a body cavity for treatment or diagnosis. These include, among others, the ablation of tissue such as fibrous plaque, thrombus, calcified plaque, and tumors, the destruction of calculi, and the heating of bleeding vessels for coagulation. Some ablation targets, such as calcified endovascular lesions, for example, can be especially difficult to ablate. The lasers used may produce either pulsed or continuous-wave light of wavelengths ranging from the ultraviolet to the infra-red.

BRIEF SUMMARY OF THE INVENTION

Various catheters, catheter tips, fiber optics, and/or light guides are provided according to embodiments disclosed herein. In various embodiments, light guides and/or catheters may have tips with various configurations that increase the energy density and/or increase the spot size of the resulting beam of light. In some embodiments catheters are provided that incorporate, for example, liquid light guides, fiber optics with diverging tips, and/or fiber optics with converging tips.

A catheter tip is provided according to one embodiment. The catheter tip may include a housing, and deflection member. The housing, for example, may be attachable to a laser catheter, and have an inner lumen configured to receive light traveling in a substantially uniform direction from the laser catheter. The deflection member may be positioned in the interior of the inner lumen, and include a proximal end, a distal end, and a tapered region. The distal end may have a diameter greater or smaller than the proximal end. The tapered region, for example, may extend from the proximal end to the distal end such that when the light contacts the tapered region, the light is diverted from its substantially uniform direction to produce a light pattern that is larger or smaller than a light pattern produced without the light diversion. In some embodiments, the deflecting member is conical in shape.

In various embodiments, the interior of the deflecting member is hollow such that a portion of the light is capable of passing through the deflecting member without being diverted. In some embodiments, the inner lumen is capable of receiving a liquid medium that flows in a substantially uniform direction that facilitates light transmission. The diverting member may be capable of diverting the liquid medium from the substantially uniform direction. In some embodiments, the diverting member may include a linear or nonlinear tapered lip or tapered tip portion or tapered tip insert. In other embodiments the inner lumen and/or the deflecting member may be constructed from a material having an index of refraction less than the liquid medium.

A catheter tip is also provided, having a housing, light-receiving means and light-diverting means. The housing may be attachable with a laser catheter and have an inner lumen with a central axis extending along the longitudinal length, of the inner lumen. The light-receiving means may receive light within the inner lumen such that the received light travels along the central axis of the inner lumen. The light-diverting means may divert the light from the direction along the central axis prior to exiting the catheter tip. The light-diverting means, for example, may be located within the inner lumen. In some embodiments, the housing has an outer diameter and the light exiting the tip produces a spot size on an object in close proximity to the catheter tip that has a diameter at least the same size as the outer diameter of the housing. In some embodiments, the light-diverting means may include a tapered tip or a tapered tip portion or a tapered tip insert.

A laser catheter is provided according to another embodiment. The laser catheter may include a proximal end, a distal end, an inner lumen, a plurality of fibers, an infusion port and a deflecting member. The inner lumen may include a central axis extending from the proximal end toward the distal end. The plurality of fibers may be configured to transmit light received at the proximal end toward the distal end. The plurality of fibers may be positioned within the inner lumen of the laser catheter. The infusion port may be configured to receive a liquid and produce a flow of the liquid through the inner lumen toward the distal end substantially along the central axis of the inner lumen. The deflecting member may be positioned within the inner lumen near the distal end. The deflecting member may be capable of diverting at least a portion of the fluid from exiting the inner lumen at the distal end from substantially along the central axis of the inner lumen.

A catheter tip is also provided according to another embodiment. The catheter tip may include a housing and a deflection member. The housing may be operable with a laser catheter and include an inner lumen configured to receive light emitted by the laser catheter. The emitted light may have a first diameter corresponding to an inner diameter of the laser catheter, and the light travels in a substantially uniform direction along the longitudinal length of the inner lumen. The deflecting member may be positioned within the housing. The deflecting member may have a proximal end and a distal end with a tapered region therebetween. The deflecting member may function to divert the received light from the uniform direction such that the light exiting the catheter tip has a second diameter which is larger than the first diameter.

BRIEF DESCRIPTION OF THE DRAWINGS

FIGS. 2A, 2B, 2C, and 2D show examples of tapered waveguides according to one embodiment.

FIGS. 8A and 8B show waveguides with proximal cylindrical ends according to another embodiment.

FIGS. 9A and 9B show various views of a waveguide with a proximal cylindrical end and a distal cylindrical end according to another embodiment.

FIGS. 13A-13C show tapered liquid light guide tips with various attachment mechanisms according to various embodiments.

Figure 1:
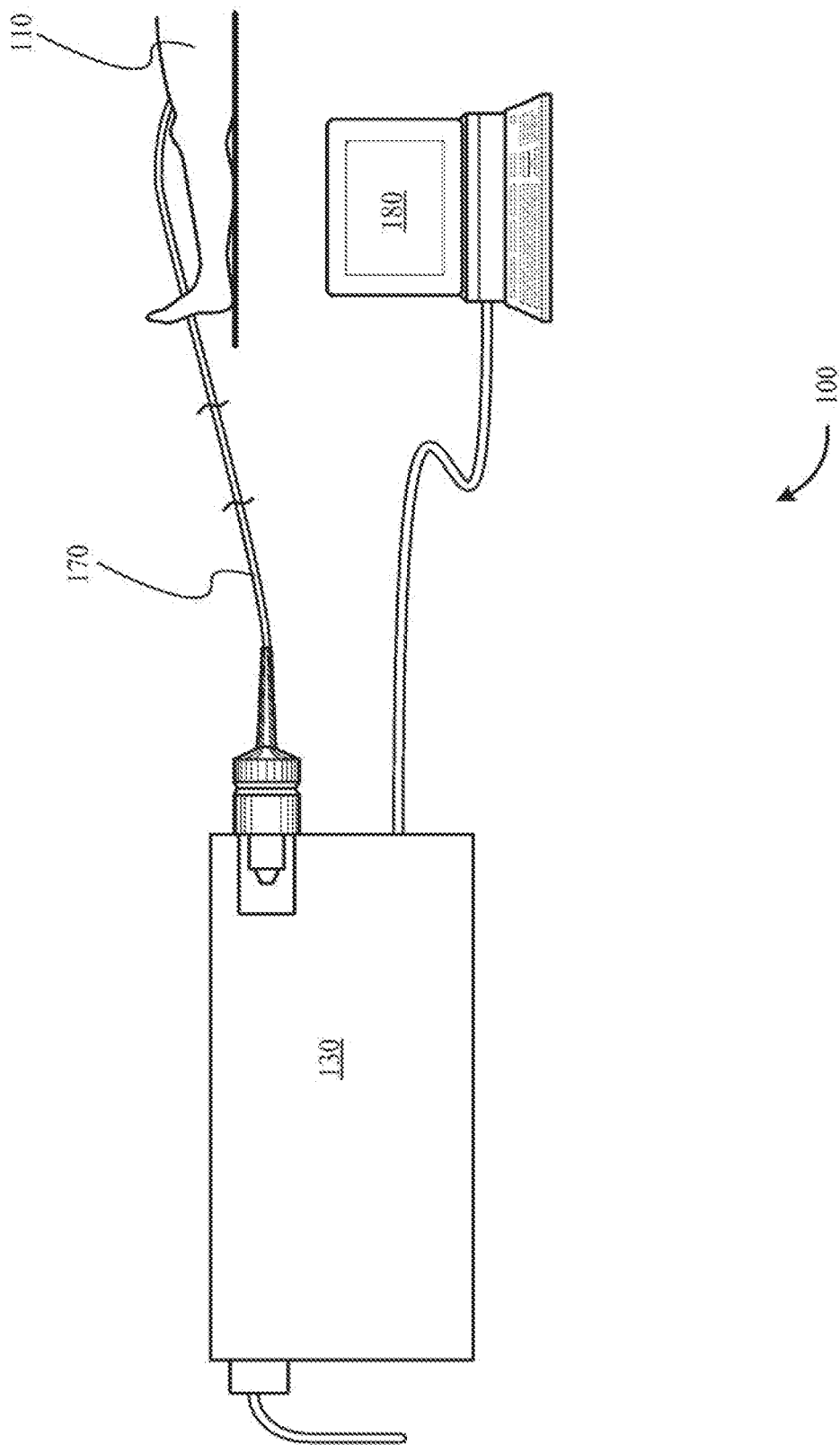
FIG. 1 shows a laser catheter system according to one embodiment.

In the appended figures, similar components and/or features may have the same reference label. Further, various components of the same type may be distinguished by following the reference label by a dash and second label that distinguishes among the similar components. If only the first reference label is used in the specification, the description is applicable to any one of the similar components having the same first reference label irrespective of the second reference label.

DETAILED DESCRIPTION

The ensuing description provides preferred embodiment(s) only, and is not intended to limit the scope, applicability or configuration of the disclosure. Rather, the ensuing description of the preferred embodiment(s) will provide those skilled in the art with an enabling description for implementing a preferred embodiment. It should be understood that various changes may be made in the function and arrangement of elements without departing from the spirit and scope as set forth in the appended claims.

Various embodiments are described throughout this disclosure. The various embodiments share a number of themes. For example, embodiments largely describe catheters and/or removable catheter tips that may have uniquely configured tips. For example, the distal tip may include a taper with a distal tip larger than the catheter body, a taper with a distal tip smaller than the catheter body, diverting tips, and/or fiber optics within a catheter with such configurations. Moreover, embodiments described herein may be used in a variety of catheters, for example, laser catheters, liquid catheters, etc. Other embodiments may be used in waveguides.

At least three major embodiments are described in detail with further descriptions of a variety of sub embodiments. These embodiments include tapered waveguides with a portion of the catheter having a tip with a larger cross section than the catheter body. Embodiments also include tapered catheters with a smaller distal tip cross section than the catheter body. Embodiments may also include liquid catheters with diverting tips. Each of these three embodiments along with various sub-embodiments and/or features are described in detail within the following three sections.

I. Tapered Waveguide Concept

In one embodiment, the present disclosure provides for tapered waveguides. According to embodiments described in this disclosure, tapered waveguides have at least one end with a circumference larger than the circumference of the waveguide body. Such waveguides provide increased exit and entrance apertures. An increased entrance aperture with respect to the waveguide body, for example, may provide an increased coupling cross-section, while maintaining a flexible waveguide body. An increased exit aperture with respect to the waveguide body, for example, may provide an increased cutting cross-section for laser catheter applications, while maintaining a flexible waveguide body. For example, a proximal end may have a circumference greater than the waveguide body, the distal end may have a circumference greater than the waveguide body, or both the distal and proximal end may have a circumference larger than the waveguide body. The taper between circumferences may be gradual of abrupt. An abrupt taper, for example, may have, for example, an infinite slope. A more gradual taper, for example, may taper between the two circumferences over a couple millimeters or up to a couple meters. A tapered waveguide may be a laserwire, fiber optic, hollow waveguide, etc. The slope of a taper is directly proportional to the amount of light lost in the taper. For example, a gradual taper provides less loss than a quicker taper.

In another embodiment, the present disclosure provides for a laser catheter comprising one or more tapered waveguides. Such a catheter may be coupled with a laser or other light source and be configured to direct light through the one or more waveguides toward a target within, for example, a human body. One or more tapered waveguides with a proximal end circumference larger than the waveguide body, according to embodiments, may provide increased coupling with the light source. In such embodiments, each waveguide may capture more light at the laser interface. One or more tapered waveguides, with a distal end circumference larger than the waveguide body, according to embodiments, may provide a cutting cross-section, which lends itself to increase ablation energy. Use of tapered waveguides may allow for more flexible catheters. In some embodiments, a single tapered waveguide may be used within a catheter.

FIG. 1 shows a laser catheter system 100 according to one embodiment. A laser 130 is shown coupled with a user interface 180. In this embodiment the user interface 180 is computer programmed to control the laser 130. The laser, for example, may be an excimer laser. The laser, for example, may also produce light in the ultraviolet range. The laser is connected with a catheter 170 that may be inserted into a vessel of the human body 110. The laser catheter system 100 may employ one or more tapered waveguides that guide laser light from the laser 130 through the catheter 170 toward a target.

FIGS. 2A, 2B, 2C, and 2D show examples of tapered waveguides 205, 206, 207, 208 according to various embodiments. These tapered waveguides 205, 206, 207, 208 may be used, for example, within the catheter 170 shown in FIG. 1. The tapered waveguide 205 shown in FIG. 2A includes a waveguide body 210, a proximal tapered waveguide end 220A, and a distal tapered waveguide end 220B. Light from a light source, such as a laser, may be received at the surface 221 of the proximal tapered waveguide end 220A and is transmitted through the waveguide body 210. The proximal tapered waveguide end is tapered from a first circumference or diameter at the junction with the waveguide body at the surface 221 of the proximal tapered waveguide end 220A to a second circumference or diameter.

FIG. 2B shows a waveguide 206 with only a proximal waveguide end 220A. FIG. 2C shows a tapered waveguide 207 with an extended end portion 225 with the proximal waveguide end 220A. FIG. 2D shows a tapered waveguide 208 with a gradual taper 265.

Generally speaking, tapered waveguides have not been considered a viable option because of light loss within the tapered portion of the waveguide. Waveguides take advantage of total internal reflection to guide light from the proximal end of a waveguide toward the distal end of the waveguide. Light within the waveguide that is incident on the walls of the waveguide at an angle less than the critical angle is internally reflected. The angle may be managed to minimize reflection losses by geometric design and by the choices of optical materials. The critical angle is defined by the materials used at the interface of the waveguide and the exterior of the waveguide. Materials are usually selected for waveguides that ensure the light within the waveguide is internally reflected to move the light through the waveguide. Light incident on a taper in the waveguide, going from a larger circumference or diameter to a smaller circumference or diameter, may be incident on the outer surface of the waveguide at an angle less than the critical angle. The critical angle is affected by the step function in the index of refraction at the boundary of the light guide medium and the confining medium. Accordingly, such light will not be internally reflected and will be lost. This loss, due to the taper, has discouraged use of tapers in waveguides. However, according to embodiments provided in this disclosure, the loss effected by such a taper may be less than losses associated with a small waveguide cross-section. Moreover, a tapered waveguide may also be less complicated than other options.

The waveguides may comprise any dimension. For example, the length 250 of the waveguides may be three to four meters according to one embodiment. The diameter 240 of the proximal tapered waveguide end may be 150 microns and the diameter 241 of the distal tapered waveguide end may also be about 150 microns. In other embodiments the diameter of each tapered waveguide end may be different. As another example, depending on the application, these diameters 240, 241 may range from 50 microns to over 1,000 microns. The waveguide body 210 may have a diameter, for example, ranging from 40 microns to 600 microns. Various other dimensions may be used without limitation. As another example, the taper dimensions 245, 246 may extend from less than 1 mm to over 5 mm. In other examples, the taper may extend over 1 meter or longer and may be as little as 10 microns. In some applications the waveguide body may be flexible.

A tapered waveguide may comprise dielectric material with high permittivity and/or index of refraction. The waveguide may be surrounded by cladding with low permittivity and/or index of infraction. Such a waveguide, for example, an optical fiber, guides optical waves therethrough by total internal reflection. Other types of optical waveguides may be such as, for, a photonic-crystal fiber, a hollow tube with a highly reflective inner surface, light pipes. A hollow waveguide may include internal surfaces covered with a polished metal or covered with a multilayer film that guides light by Bragg reflection. An optical fiber waveguide, for example, may comprise plastic, silica, or any other glass. In some applications, such as when used with an ultraviolet light source, the optical fibers may have a high OH or high saline material.

The optical waveguide may comprise material that is well matched to the type of light it guides. For example, an ultraviolet waveguide may be comprised of material that is transmissive to ultraviolet light. For example, the waveguide may be an optical fiber with a high OH or saline content. As another example, an infrared waveguide may have a low OH content. According to another embodiment, the waveguide may also comprise plastics, quartz, and/or sapphire. The waveguide may, for example, be cylindrically shaped or may comprise an elongated shape with an oval, square, hexagonal, octagonal, triangular, etc cross section. According to another embodiment, the waveguide may be hollow. In yet another embodiment, the waveguide may comprise multiple geometries that vary over the length of the waveguide.

Figure 3:
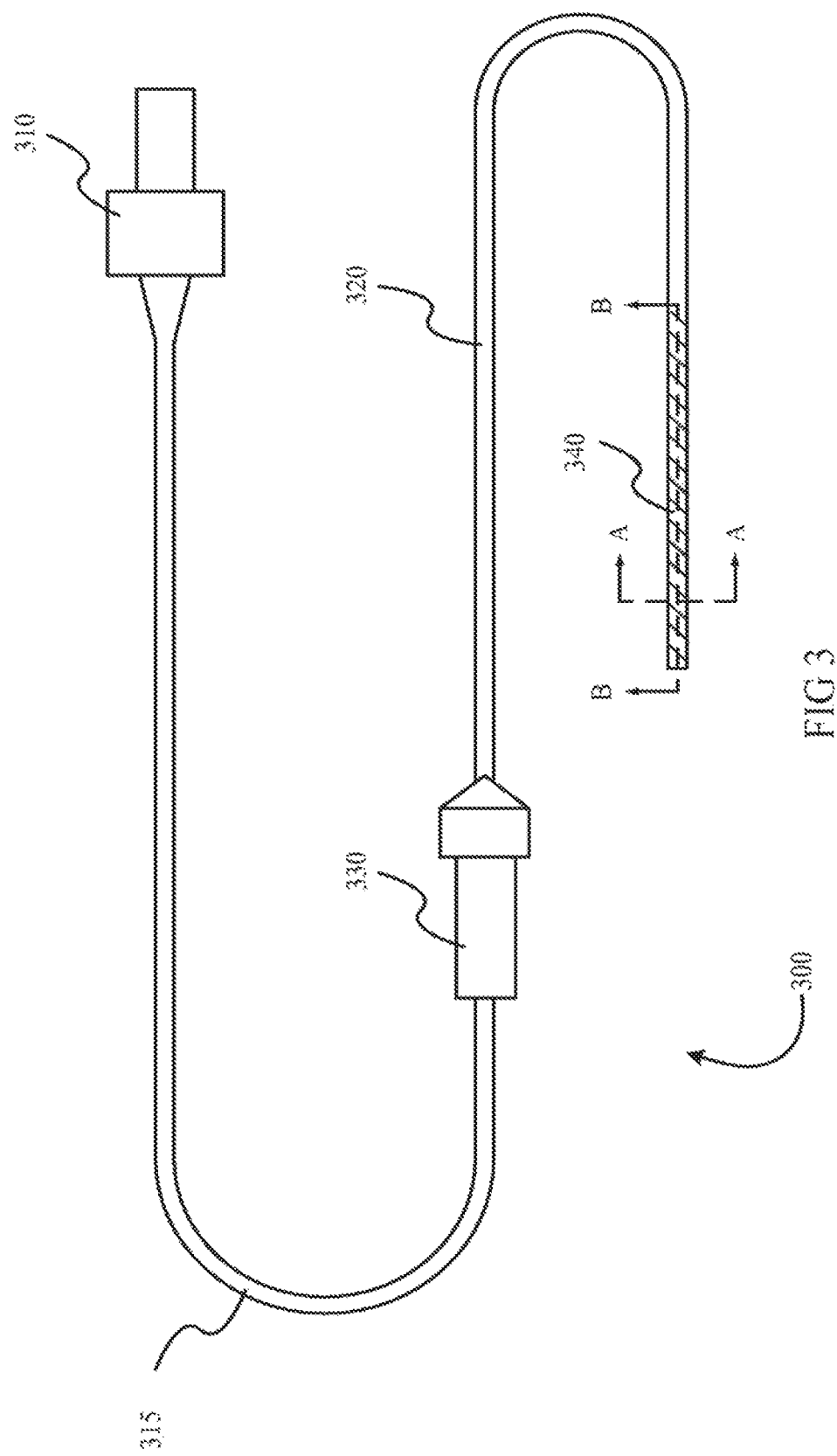
FIG. 3 shows a laser catheter according to another embodiment.

FIG. 3 shows a laser catheter 300 according to another embodiment. According to this embodiment, the laser catheter 300 includes a laser coupler 310 that may be coupled with a laser (as shown in FIG. 1). The laser catheter 300 includes a tail tube 315 and torque handle 330. The torque handle 330 may be used to rotate the catheter body in order to steer within discrete locations of the body vasculature. The catheter body portion may include an internal lumen for introduction over a guidewire. The hypotube 320 construction, for example, may provide sufficient torque, stiffness and pushability to the catheter 300 in situations where it is not configured to be introduced over a guidewire. The distal end 340 of the catheter may include a flexible distal section.

The hypotube, for example, may be 180 to 300 cm in length and have a diameter of about 0.014 inches.

The distal end 340 may include any of the waveguides described in association with embodiments presented in this disclosure. The tapered waveguide may have a tapered distal and/or proximal section as described in any of the embodiments of the invention. Moreover, the distal end 340 may include a waveguide with large cylindrical distal ends and/or proximal ends as will be described in association with FIGS. 8A, 8B, 9A, and 9B. A waveguide may extend through the hypotube 320 and tail tube 315. Accordingly, the proximal end of the waveguide may be coupled with the laser coupler 310. The proximal end of the waveguide may also be configured to receive laser light at the laser coupler 310 when the laser catheter is coupled with a laser. A larger cross-section at the proximal end of a waveguide may provide, for example, a larger laser light-collecting surface area at the laser coupler 310. In yet other embodiments, for example, like those shown in FIGS. 16-20, the distal end may include a tapered tip or a tapered portion or a tapered insert that diverges light outwardly from the catheter diameter.

In some embodiments a taper in the waveguide may occur within the tail tube 315, torque handle 330, laser coupler 310, and/or a combination thereof. In some embodiments, a taper from a larger circumference or diameter waveguide to a smaller circumference or diameter waveguide gradually occurs throughout the portions or the entire tail tube 315. In other embodiments, a taper may occur less gradually, for example, within the laser coupler 310, or the torque handle 330. In yet other embodiments, a taper may occur within the hypotube 320. Various other embodiments may envision tapers within other portions of a waveguide without limitation.

Figure 4:
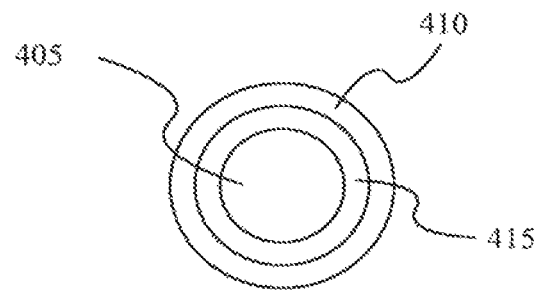
FIG. 4 shows a cross-section of a laser catheter according to another embodiment.

A cross-section of the flexible distal section 340 cut along section A-A of FIG. 3 is shown in FIG. 4 according to tone embodiment. As shown, a waveguide core 405 is surrounded by the hypotube 410. The hypotube 410 may be adhered to the waveguide core 405 with epoxy 415. The waveguide core 410 may comprise one optical fiber or a plurality of optical fibers bundled together. Various other waveguides may be used within the optical core of the laser catheter, for example, hollow waveguides, multiple core waveguides, etc.

Figure 5:
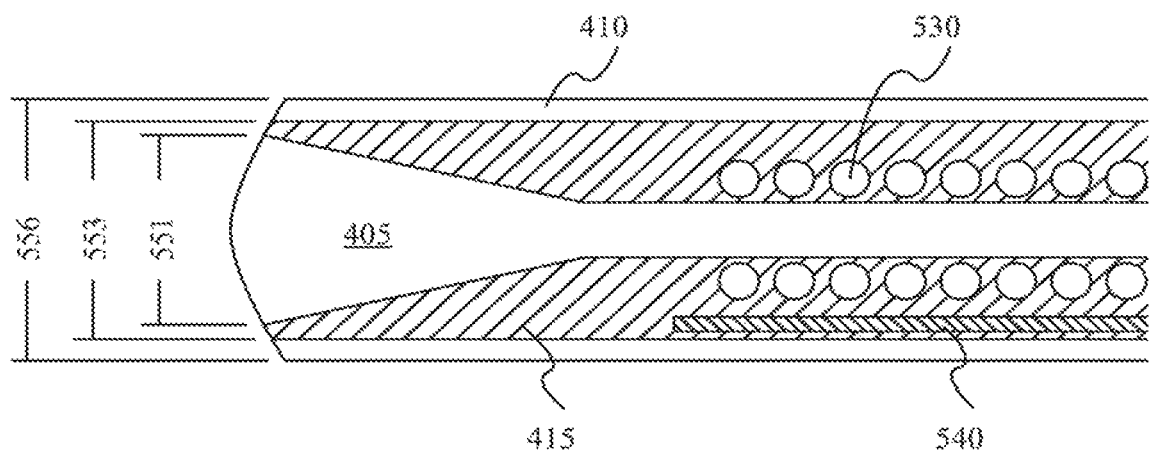
FIG. 5 shows a cross-section of the distal end of a laser catheter with a tapered end according to another embodiment.

FIG. 5 shows another cross-section of the distal end of the laser catheter 300 cut along section B-B of FIG. 3, according to one embodiment. A tapered waveguide 405 is shown surrounded by epoxy 415 and a hypotube 410. According to another embodiment, the distal end of the laser catheter 300 may include a radiopaque coil 530 or marker band. The coilband 530 or marker band of various shapes and sizes may be comprised of a radiopaque material such as platinum-iridium or other suitable material and may be disposed near the distal tip of the catheter to aid in fluoroscopic or other visualization of the placement of distal tip. In some embodiments, the hypotube may also include a shape ribbon 540. The shape ribbon, for example, may have a constant width. In some embodiments, the ribbon of material may have a width that continuously and/or smoothly increases toward the proximal end of the hypotube. In some embodiments, the ribbon may have discrete sections where the width of each successive section is larger than the width of the adjacent distal section.

Figure 6A:
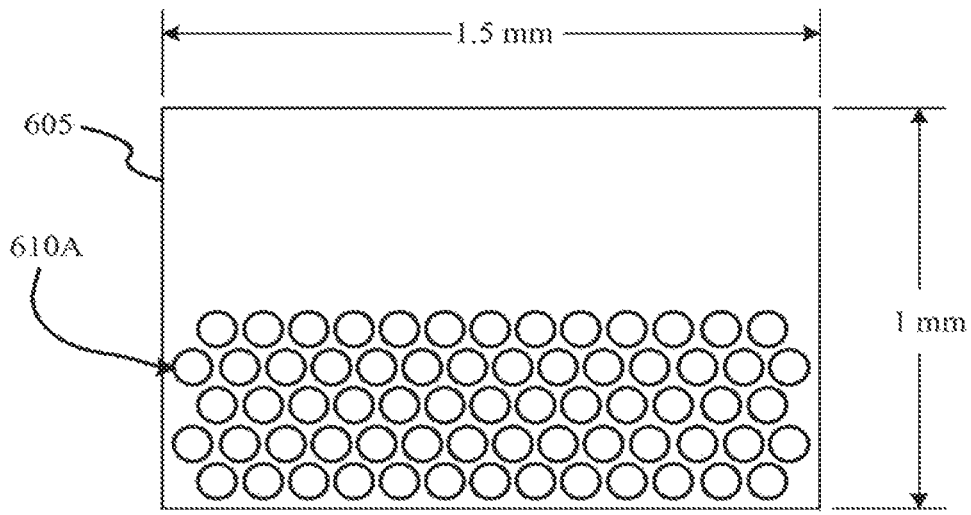
FIG. 6A shows a bundle of untapered waveguides covering a laser light profile according to another embodiment.

In some embodiments of the invention a plurality of tapered waveguides may be used to direct laser light from the proximal end to the distal end of a laser catheter. FIG. 6A shows a cross-section of a plurality of waveguides without tapered ends 610A packed within a laser profile 605. A laser profile may have a fixed profile as shown in the figure. In this example, the laser profile 605 has a fixed profile of about 1 mm by 1.5 mm. In this example, 67 waveguides are packaged within a laser catheter. The number of waveguides used within a single catheter may be limited by the various design constraints such as, for example, desired flexibility of the laser catheter, the circumference or diameter of each waveguide, die required energy output, etc. In the example shown in FIG. 6A, the 67 waveguides with diameters of approximately 50 microns to meet the desired design constraints of the laser catheter.

Figure 6B:
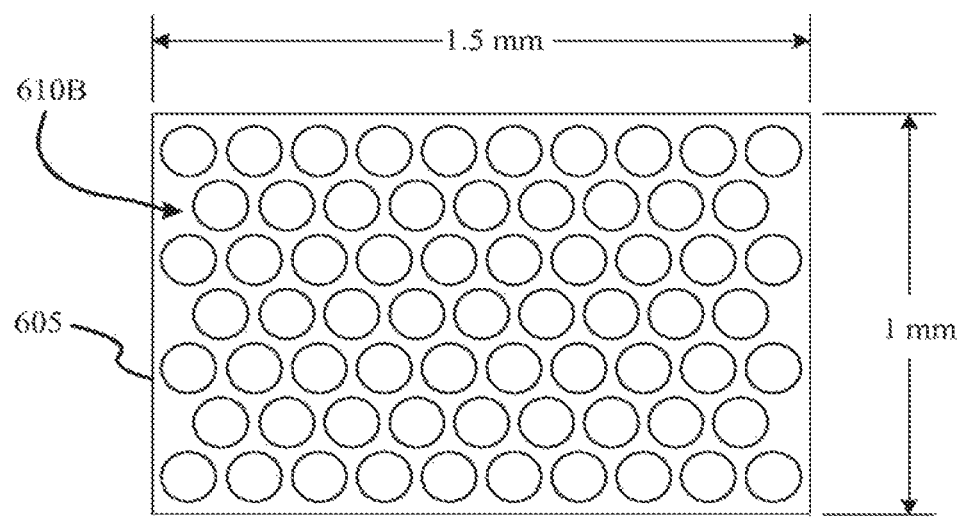
FIG. 6B shows a bundle of tapered waveguides covering a laser light profile according to another embodiment.

As shown, such waveguide cross-sections and the number of waveguides cover less than half of the laser profile 605. Accordingly, more than half the laser energy is lost prior to entry at the waveguides. The number of waveguides could be increased to capture more laser energy, but such an increase would limit the flexibility of the laser catheter. Moreover, focusing of the laser light from the full profile to a profile focused on a smaller profile using optical elements may be used, but any optical element is inefficient and introduces losses in the laser energy. Tapered waveguides, as described in embodiments of this disclosure, may be used to collect more laser energy by increasing the waveguide cross-section at the proximal end of the waveguide, as shown in FIG. 6B, without sacrificing flexibility throughout the laser catheter body. Moreover, in another embodiment of the invention, a taper at the distal end of a waveguide may be used, with or without a proximal taper, to increase the cutting cross-section area of the distal end of the waveguide without interfering with the tractability of the laser catheter. While the packing configurations shown in FIGS. 6A and 6B are rectangular, the packing configuration is not limited thereby. The packing configuration may be round, hexagonal, or scattered depending on such things as the catheter and/or laser profile cross sections.

Figure 7A:
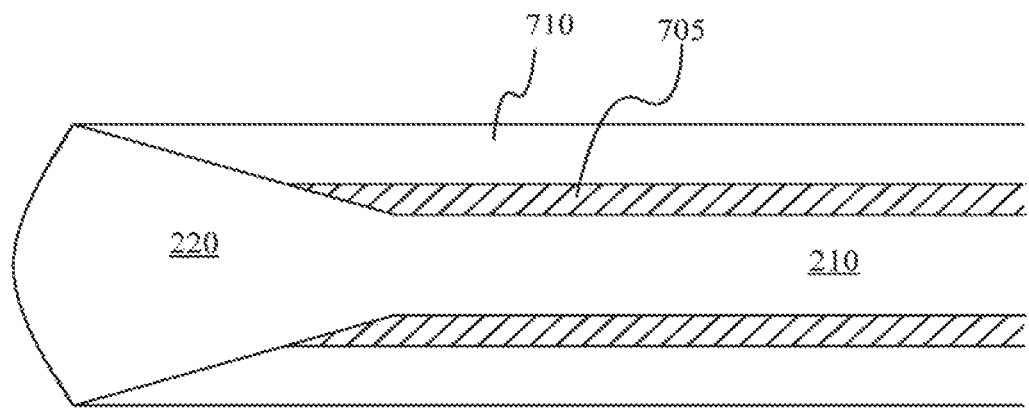
FIGS. 7A, 7B and 7C show cross-sections of tapered waveguides according to various embodiment.
Figure 7B:
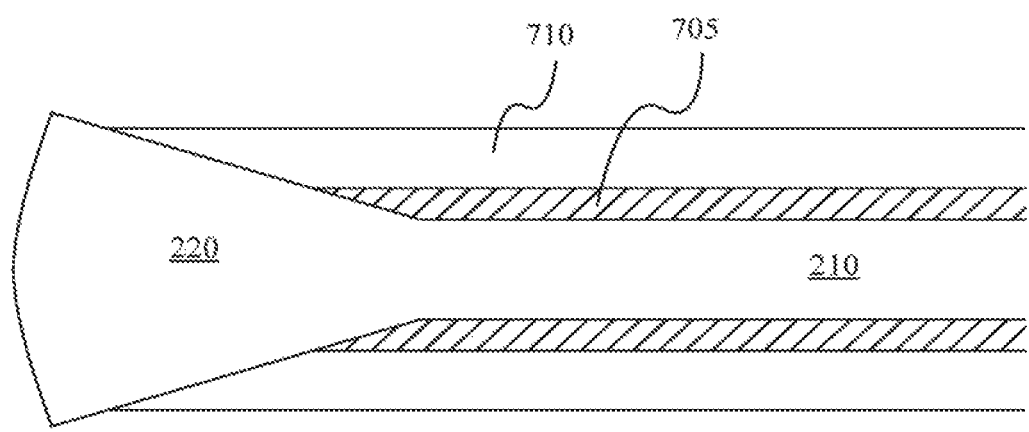
Figure 7C:
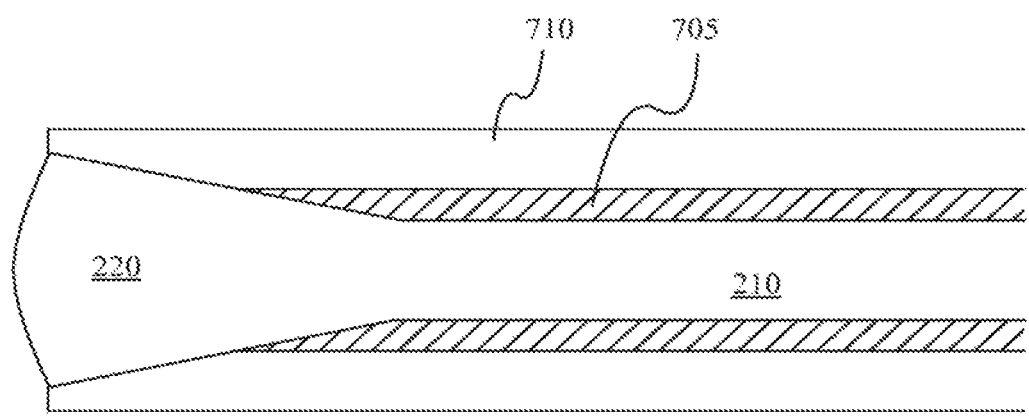

FIGS. 7A, 7B, and 7C show cross-sections of tapered waveguides according to various embodiments. FIG. 7A shows a waveguide with a waveguide body 210 and a tapered end 220. The waveguide has a hypotube 710 surrounding the waveguide and coupled with the waveguide using epoxy 705. In FIG. 7A the hypotube 710 diameter is the same as the diameter of the largest part of the tapered end 220. Thus, the waveguide tapers to the same diameter of the hypotube 710.

In FIG. 7B the hypotube 710 diameter is less than the diameter of the largest part of the tapered end 220. Thus, the waveguide tapers to a diameter larger than the diameter of the hypotube 710. In FIG. 7C the hypotube 710 diameter is greater than the diameter of the largest part of the tapered end 220. Thus, the waveguide tapers to a diameter smaller than the diameter of the hypotube 710.

FIG. 8A shows a waveguide 800 with a proximal cylindrical end 805 attached with a waveguide body 810 according to another embodiment. FIG. 8B shows a three dimensional view of a waveguide with a proximal cylindrical end 805. The cylindrical may be comprised of waveguide material with a larger diameter, such as a larger diameter fiber. As shown, one way to construct such a waveguide is to fabricate a hole 815 within a cylinder that is dimensioned to securely receive the waveguide body 810. The hole 815 may be fabricated, for example, during production of the cylinder, or by drilling, or any other means. Glue, such as epoxy, may be used to secure the waveguide body 810 with the cylinder 805. A proximal cylinder end 805 may increase the cutting end of the waveguide similar to using a tapered proximal end. The cylinder 805 may, according to another embodiment, incorporate a tapered light-guide.

FIG. 9A shows a waveguide with a proximal cylindrical end 920 and a distal cylindrical end 805 according to another embodiment. The proximal cylindrical end 920 may be used to increase the energy captured from a laser. The most proximal surface 930 may be coated with a material that permits exterior light to enter the proximal cylindrical end 920. The more distal surface 940 may be coated with a reflective surface. Thus, light entering the proximal cylindrical end 920 may only exit the cylinder through the waveguide body 810. Light may reflect back and forth within the proximal cylindrical end 920 until the light enters the waveguide body 810. The cylinder 805 may, according to another embodiment, incorporate a tapered light-guide.

FIG. 9B shows another waveguide with a proximal cylindrical end 920 and a distal cylindrical end 805 according to another embodiment. In this embodiment, the more distal surface 945 of the proximal cylindrical end is concave and reflective. This surface focuses the light toward the more proximal surface 935, which may, according to one embodiment, be coated with a material that permits exterior light to enter the proximal cylindrical end 920 but reflects light that is incident from within the cylindrical end 920. In another embodiment, the more proximal surface 935 may include a single reflective portion located near the area where light may be focused by the concave more distal surface 943. Thus, according to this embodiment, light entering the more proximal surface 935 is reflected and/or focused by the more distal surface 945 and then reflected and/or focused through the waveguide body 810 by the more proximal surface 935. A concave surface may be used on either the distal or proximal ends of the waveguide.

II. Tapered Catheter Tip

Embodiments described throughout this disclosure provide for tips, sheaths, catheters, and/or devices that increase the energy density of a laser catheter. Some embodiments use tapered liquid light guides that decrease the beam cross-section of laser light in order to increase the energy density. Such energy density increases may be useful for ablating stubborn lesions, occlusions, obstructions, etc. Moreover, many of the embodiments are directed to devices that may be accessories to a standard laser catheter. For example, various embodiments include detachable and/or replaceable catheter tips and/or sheaths.

A tapered catheter tip is provided according to one embodiment. Such a tapered catheter tip may be coupled with a laser catheter. The taper provides a decrease in the laser spot size and, therefore, an increase in the energy density of laser light. Such tips, in one embodiment, may be constructed of material with an index of refraction which is lower than the liquid medium on the inner lumen at the tip in order to induce internal reflection from within the liquid core. In another embodiment, a tip may be constructed of a material that provides low light attenuation. In some embodiments the laser catheter may provide light in the ultraviolet range. Moreover, the tapered catheter tip may direct a liquid medium from the proximal end of the tip toward the distal end of the tip.

In use, a user may be performing laser ablation within a patient using a liquid light guide laser catheter. In this example, the laser catheter may operate with 308 nm UVB light and the laser catheter may use a range of solutions such as NaCl solution as the liquid light guide medium. At some point in the procedure the physician may encounter a target that is difficult to ablate with the laser catheter, such as calcified endovascular lesions. In such a case, an increased, laser density may provide better ablation. Accordingly, the physician may remove the laser catheter, and attach a tapered catheter tip. The tapered catheter tip narrows the spot size of the laser light emanating from the laser catheter while transmitting roughly the same laser energy. The physician may then reinsert the laser catheter and ablate the difficult target using the tapered tip. Following ablation, the physician may remove the tip or continue ablation with the tapered tip.

Some embodiment provide a tapered catheter sheath. Such a catheter sheath may be an elongated tubular structure that accepts a laser catheter through much of the elongated portion thereof. In other embodiments the elongated tubular structure accepts a laser catheter through all, most of all, or a portion thereof. In some embodiments the catheter sheath is tapered at the distal end to decrease the spot size of the laser light. In other embodiments the catheter sheath may include an infusion port that provides biocompatible fluid delivery through the sheath toward the distal end of the sheath. In another embodiment, a sheath may be constructed of a material that provides low attenuation of light. In some embodiments the sheath or at least a tapered portion, of the sheath may be constructed of material with a low index of refraction in order to induce total internal reflection. In some embodiments the laser catheter may provide light in the ultraviolet range.

Figure 10:
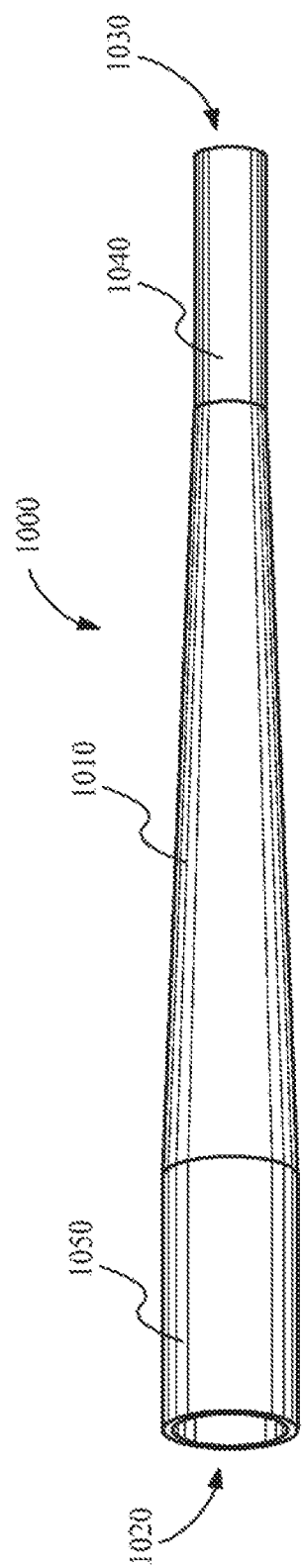
FIG. 10 shows a tapered liquid light guide tip according to one embodiment.

FIG. 10 sows a tapered liquid light guide tip 1000 according to one embodiment. The liquid light guide tip 1000 includes a distal end 1030 and a proximal end 1020. In this embodiment both the distal end 1030 and the proximal end 1020 include apertures. As shown in the figure the tip includes a tapered portion 1010 between the proximal end 1020 and the distal end 1030. In some embodiments, the proximal end 1020 of the tapered liquid light guide tip may be coupled with a laser catheter, a liquid light guide, or both.

Figure 11:
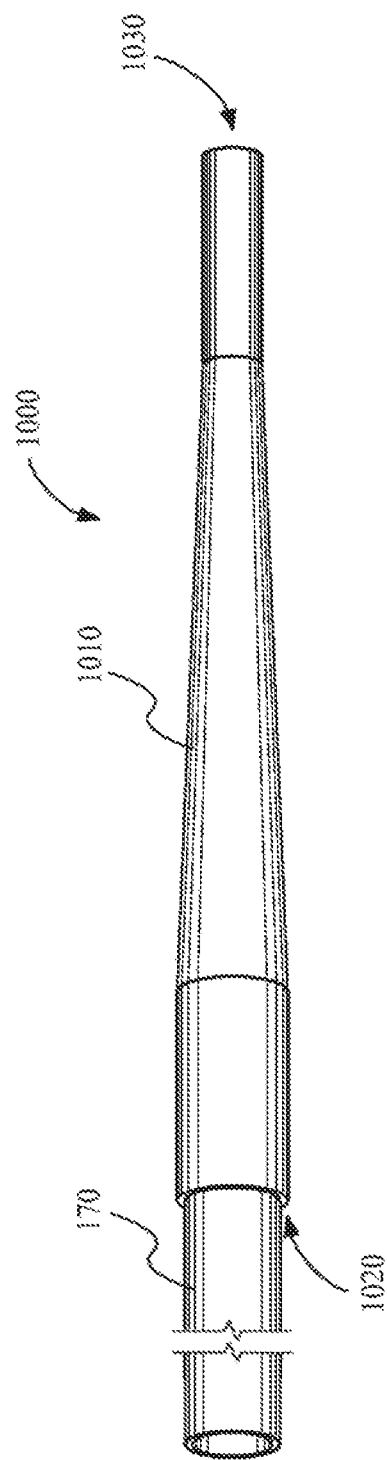
FIG. 11 shows a tapered liquid light guide tip coupled with a laser catheter according to one embodiment.

FIG. 11 shows the proximal end 1020 of a tapered liquid light guide tip 1000 coupled with a laser catheter 170 according to one embodiment. Only a portion of the laser catheter 170 is shown. When coupled with a laser catheter 170, the liquid light guide tip 1000 may direct laser light with a more concentrated spot beam toward a target from the distal end 1030. In doing so, the energy density of the light incident on a target from the laser catheter 170 through the liquid light guide tip 1000 is increased due to the decrease in spot size. The laser catheter 170 may also provide a biocompatible fluid that flows through the liquid light guide tip 1000 from the proximal end 1020 toward the distal end 1030. In order to decrease the spot size of the laser beam through the tip, total internal reflection must be maintained through the taper 1010 of the liquid light guide tip 1000. Total internal reflection can be maintained when the biocompatible fluid has an index of refraction greater than the index of refraction of the lining of the tubing.

The biocompatible fluid, in some embodiments, may include a saline solution. In other embodiments the biocompatible fluid may include $MgCl_2$, NaCl, CaCl, etc. In other embodiments the biocompatible fluid may include a solution comprising, for example, Ca, Mg, Mn, Ni, Cl, and/or Co. In some embodiments, the biocompatible fluid may include lactated Ringer's solution. The lactated Ringer's solution, for example, may come from sodium chloride (NaCl), sodium lactate ($NaC_3H_5O_3$), calcium chloride ($CaCl_2$), and/or potassium chloride (KCl). Those of skill in the art will recognize that other combinations of salts may be used. In some embodiments, magnesium chloride and lactated Ringer's solution have good biocompatibility (e.g., low toxicity) as well as good light transmission characteristics at the 308 nm wavelength. The biocompatible fluid may be tailored to the wavelength of light produced by the laser. For example, waveguides including a biocompatible fluid of approximately 15% to approximately 60% by weight $CaCl_2$ transmit light well in the infrared, but only partially in the ultraviolet region. There are many types of biocompatible fluids that may be used without limitation. Moreover, embodiments described herein are not limited to specific biocompatible fluid.

The body and/or walls of the tapered liquid light guide tip 1000 may comprise any low index material without limitation. For example, a material with an index or refraction below the index of refraction of water, approximately 1.4 at the 308 nm wavelength. These materials may include, for example, Teflon AF2400 tubing made by DuPont. In other embodiments, the walls may include any fluoropolymer, such as, for example, Hyflon® PFA or MFA, FEP, KEL-F, Teflon PFA, Tefzel, Fluon, Tedlar, ECTFE, PVDF, PCTFE, FFKM, Kalrez, Viton, Krytox, and 3M THV-500. Polyethylene, PVC, polycarbonate and/or other plastics may be used in some embodiments.

The tapered liquid light guide tip 1000 may include portions without a taper. For example, as shown in FIG. 10, the tip 1000 may include an extended portion 1050 near the proximal end and/or a extended portion 1040 near the distal end. While the extended portion 1050 and/or the distal aperture are shown with a circular cross section, any shape may be used. For example, the cross section may be oval or polygon shaped. Moreover, in another embodiment, the distal end may taper directly to the distal aperture 1030 without a substantially extended portion. In another embodiment, the tip may be substantially cone shaped. In such an embodiment, the tip may have substantially no extended portions.

Figure 12:
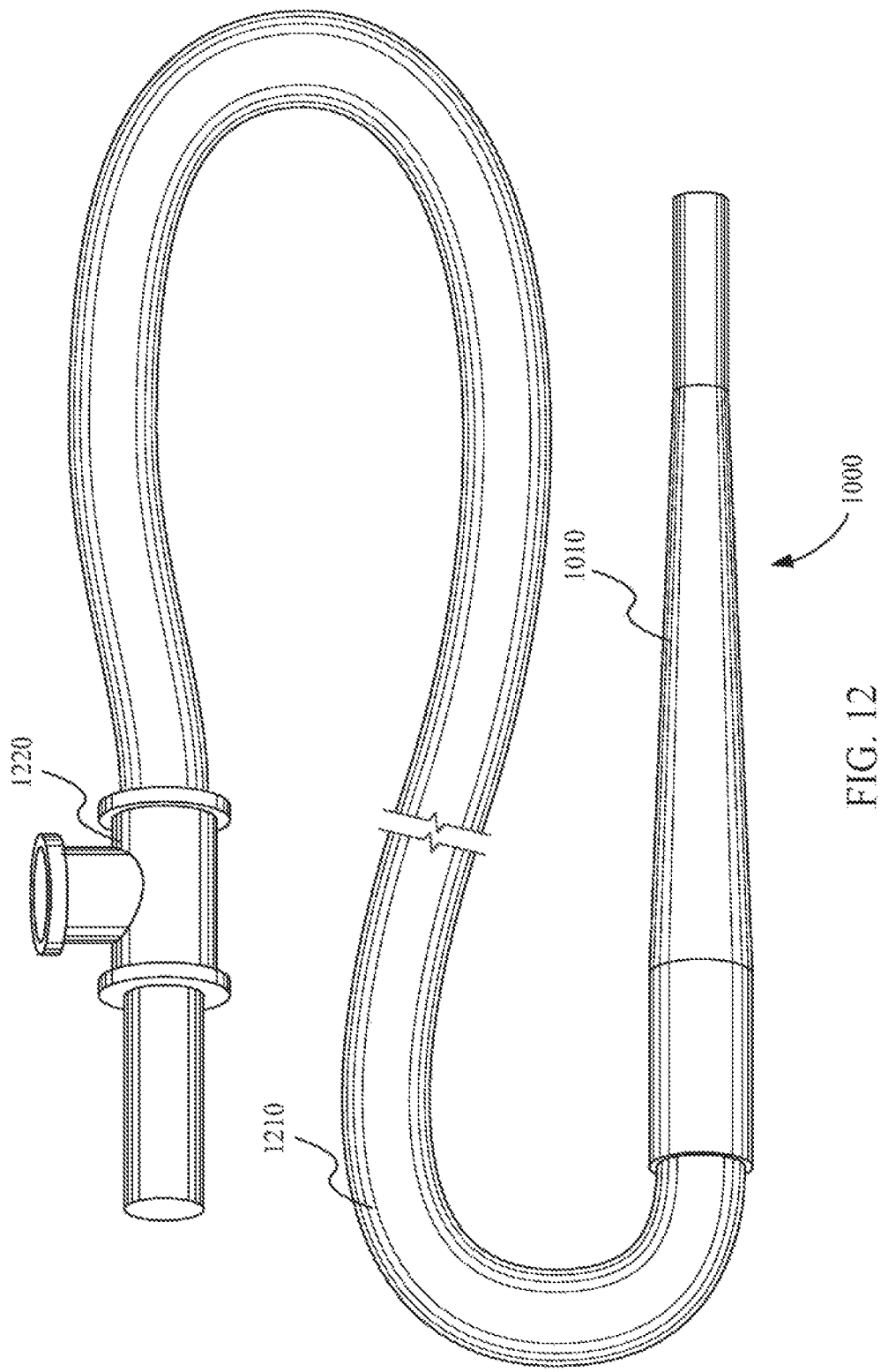
FIG. 12 shows a laser catheter coupled with a tapered liquid light guide tip according to one embodiment.

FIG. 12 shows a laser catheter 1210 coupled with a tapered liquid light guide tip 1000 according to one embodiment. The laser catheter 1210 also includes an infusion port 1220 for introducing a biocompatible material into the laser catheter 1210. The biocompatible material may act as a light guide within the laser catheter that channels light from the proximal end through the liquid toward the distal end. The tapered liquid light guide tip 1000 includes a tapered portion 1010.

FIGS. 13A-13C show tapered liquid light guide tips with various attachment mechanisms according to various embodiments. FIG. 13A shows an attachment mechanism such that a ring 1310 on the inside of the tip catches a groove on the catheter according to one embodiment. In some embodiments, at least a portion or all of the attachment mechanism comprises a shape-memory material that shrinks when heated to about the body temperature. Shrinking may more tightly secure the tip to the laser catheter when used within a body. In FIG. 13B a ring 1320 is on the exterior of the laser catheter and the groove is on the interior of the tip 1000 according to another embodiment. FIG. 13C shows the tip with threads 1340 on the interior and the laser catheter with threads 1330 on the exterior. Of course, the threads may be on the exterior of the tip and the interior of the laser catheter according to another embodiment. Various other attachment mechanisms may also be used without deviating from the spirit and scope of this disclosure. For example, clips, detents, rings, washers, pins, bushings, o-rings, etc., may be used as part of the attachment mechanism. In some embodiments, the tapered liquid light guide tip may be attached using an X-Ray contrast medium, a sticky material or any adhesive.

Figure 14:
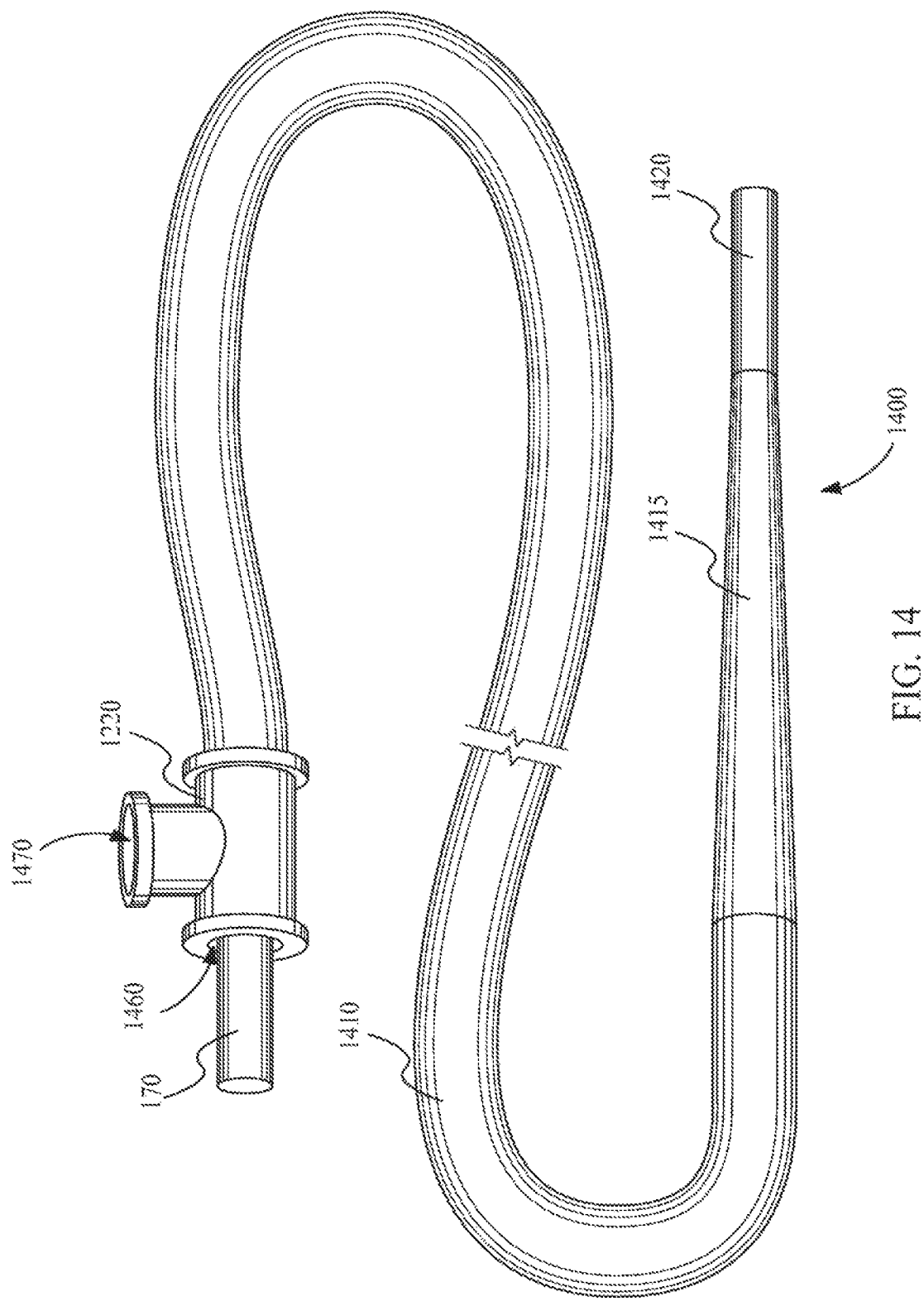
FIG. 14 shows a tapered liquid light guide sheath according to one embodiment.

FIG. 14 shows a tapered liquid light guide sheath 1400 according to another embodiment. The liquid light guide sheath 1400 may include an elongated tubular body 1410, a tapered portion 1415, a distal aperture, an inner lumen, and an infusion port 1220. The infusion post 1220 includes a catheter port 1460 that receives a laser catheter 170 or other light channeling device. The catheter port is configured to allow a catheter, such as a laser catheter, to be fed into the inner lumen of the sheath 1400. The sheath 1400 may also include a fluid port 1470 that may be coupled, for example, with a biocompatible fluid delivery device. The fluid port 1470 may receive biocompatible fluid that flows through the inner lumen of the sheath 1400. The biocompatible fluid may be used as a light guide within portions of the sheath. In some embodiments, the liquid light guide sheath may include a distal extended portion 1420, while in other embodiments the sheath tapers substantially directly to the distal aperture.

The tapered liquid light guide sheath 1400 may be used to direct laser light from a catheter and biocompatible fluid toward a target. The laser catheter 170 may slide within the inner lumen from the infusion port 1220 toward the distal end. Portions of the sheath 1400 may act as a liquid light guide directing light from the laser catheter through a distal aperture toward a target. Accordingly, in some embodiments, portions of the tapered liquid light guide sheath 1400 may comprise a low index material and/or a low attenuation material. The type of material chosen as well as the type of biocompatible fluid used within the light guide may be chosen based on the wavelength of light produced by the laser catheter.

III. Diverting Catheter Tip

Embodiments described herein also provide for diverting catheter tips. These diverting catheter tips may be provided in a number of combinations. For example, the diverting catheter tips may include diverting tip attachments that can be coupled with the distal end of a catheter. As another example, diverting catheter tips may also be integral with die distal tip of a catheter. Such diverting catheter tips may be used with liquid catheters and may divert the liquid as it exits the distal end of the catheter. Liquid catheters, in some embodiments, use a liquid medium as part of a light guide to transmit light through at least a portion of the catheter toward the distal end of the catheter. Diverting catheter tips expand the exit diameter of the distal catheter tip and, in some embodiments, may provide an increased spot size. Increasing the spot size of emitted laser light may be useful for creating ablations substantially the same size or larger than the outer diameter of the laser catheter.

Figure 15A:
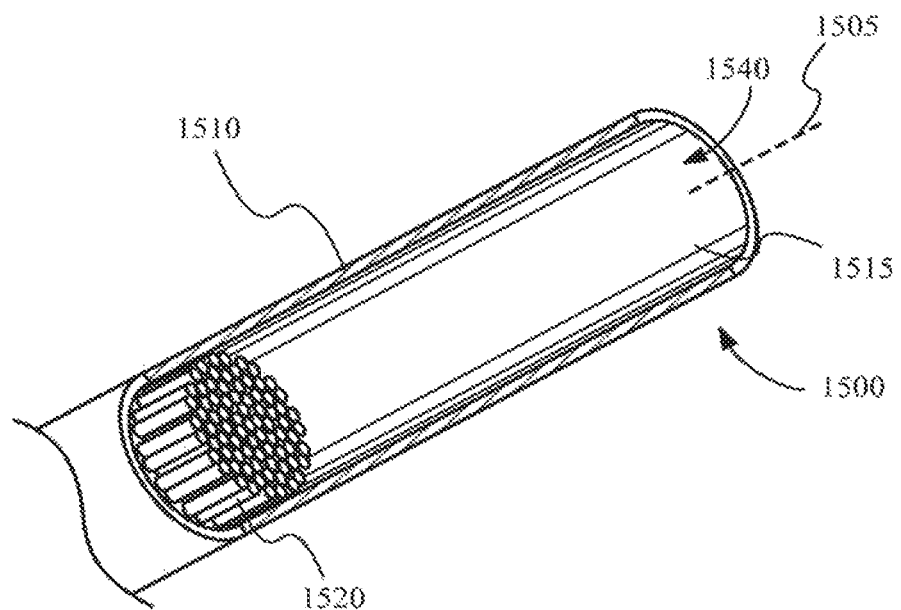
FIG. 15A shows an example of the distal end of a laser catheter incorporating a liquid light guide according so one embodiment.

FIG. 15A shows an example of the distal end of a laser catheter 1500 incorporating a liquid light guide according to one embodiment. Such catheters may include a sheath 1510 having an inner lumen 1515 housing a fiber-optic bundle 1520 capable of transmitting light. The fiber-optic bundle 1520, in some embodiments, may be arranged to terminate short of the catheter's tip such that a hollow portion 1540 is formed toward the catheter's tip. In some embodiments, a liquid medium may be used as a light guide in conjunction with the fiber optic bundle. For example, a biocompatible liquid may flow through the catheter out the distal end of the catheter. The liquid may transmit light from at least the distal, ends of the fiber optic bundle through the hollow portion 1540 of the catheter tip to facilitate in light transmission. The liquid medium may have an index of retraction greater than the inner lumen of the laser catheter in order to induce total internal reflection as light travels through the distal tip. In addition, the liquid medium may also have a low attenuation for UV light. The liquid medium may flow through the laser catheter between the fibers of the fiber-optic bundle and fill the hollow portion 1540 of laser catheter 1500 and flow toward the distal aperture. The internal reflection of the light within the inner lumen acts to channel the light along the central axis 1505 of the inner lumen 1515. Upon exiting the laser catheter, light generally continues along a path substantially parallel with the distal tip.

Figure 15B:
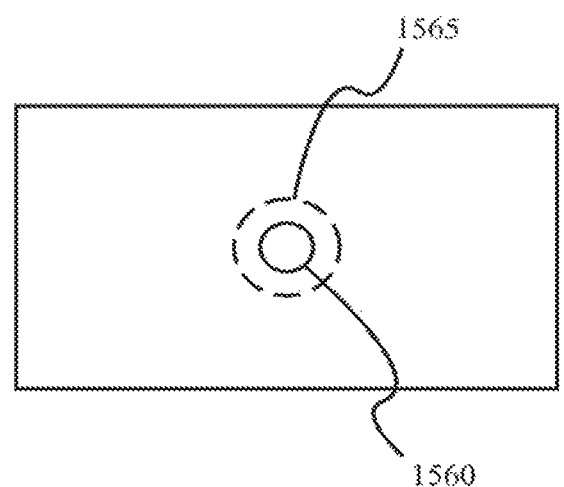
FIG. 15B shows an example of a laser spot size using the laser catheter shown in FIG. 15A.

FIG. 15B shows an example of a laser spot size 1560 using the laser catheter shown in FIG. 15A. As shown the spot size 1560 is smaller than the outside diameter 1565 of the laser catheter. The catheter shown in FIG. 15A may be used to ablate obstructions. Such ablations, however, will conform largely to the spot size 1560. However, even with such an ablation, the laser catheter may not proceed through the ablation because the diameter of the catheter is larger than the ablation.

Figure 16A:
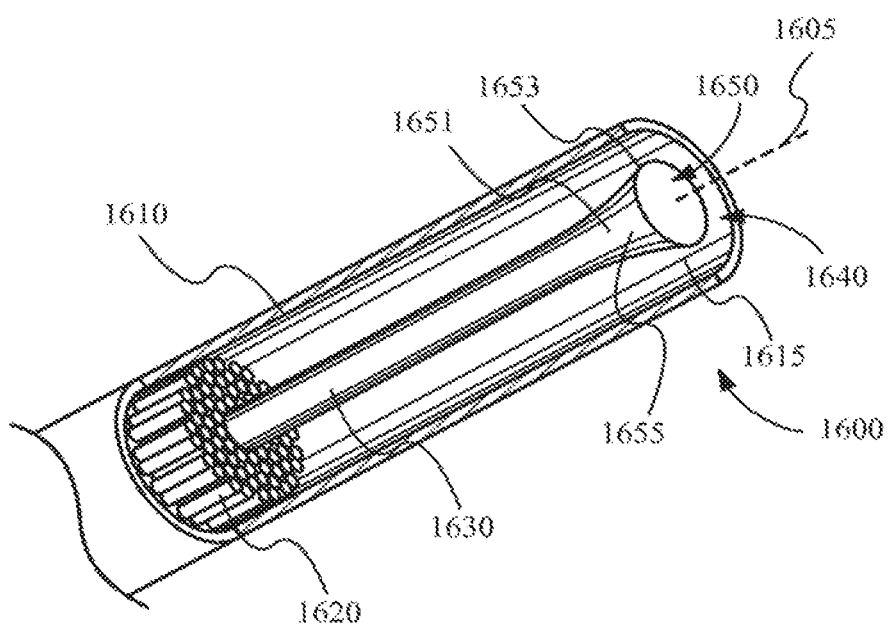
FIG. 16A shows an example of the distal end of a laser catheter incorporating a liquid light guide and diverting cone according to one embodiment.

FIG. 16A shows an example of the distal end of a laser catheter 1600 incorporating a liquid light guide and diverting tip 1650 according to one embodiment. The laser catheter 1600 is shown having a sheath 1610, an inner lumen 1615, a fiber-optic bundle 1620, a central optical fiber 1630, a hollow portion 1640, and a diverting tip 1650 coupled with the central optical fiber 1630. In some embodiments, the fiber-optic bundle 1620 terminates short of the catheter tip. In some embodiments, the fiber optic bundle terminates approximately 5 cm short of the tip. In other embodiments, the fiber optic bundle terminates, less than, for example, 1 cm, 2 cm, 3 cm, 4 cm, 6 cm, 7 cm, 8 cm 9 cm or 10 cm from the tip.

The laser catheter 1600 may partially or completely use a liquid medium as light guide. The figures show catheters that partially use liquid as a light guide. However, catheters may also use a liquid light guide without fiber optics. As shown in the figures, the liquid medium may be introduced within the catheter and travel between the fibers within the fiber optic bundle 1620 and fill the hollow space between the tip and fiber optic bundle. Light may be conducted along the way. The liquid, as it flows through the catheter, acts as a light guide directing light toward the distal end of the catheter. The liquid medium may include any biocompatible solution, such as NaCl. In some embodiments, the liquid medium may have a low attenuation for UV light, such as light emitted from an Excimer laser. The laser catheter 1600 is further shown having a diverting tip 1650 coupled with central optical fiber 1630. Sheath 1610 and diverting tip 1650 may be made from the same material to induce internal reflection within the inner lumen. For example, in some embodiments, these material may include Teflon AF2400 tubing made by DuPont. In other embodiments, the materials may include any fluoropolymer, such as, for example, Hyflon® PFA or MFA, FEP, KEL-F, Teflon PFA, Tefzel, Fluon, Tedlar, ECTFE, PVDF, PCTFE, FFKM, Kalrez, Viton, Krytox, and 3M THV-500, polyethlyene, PVC, polycarbonate and/or other plastics.

As shown, the diverting tip 1650 may have a proximal end 1651 that is smaller in diameter than the distal end 1653 with a tapered region 1655 extending therebetween. The proximal end 1651 may be fitted and/or secured with a central optical fiber 1630. In other embodiments the diverting tip 1650 may be integral or part of the central optical fiber 1630. In some embodiments, the diverting tip 1650 may be permanently or removably attached to the central optical fiber 1630. In other embodiments, the diverting tip 1650 may be positioned within the inner lumen 1615 so that the diverting tip intersects at least a portion of the flow of the liquid from the inner lumen. In such a position, with minimal light loss, she tapered region 1655 acts to divert/deflect liquid and/or light that contacts the tapered region from a path corresponding with the inner lumen's central axis 1605.

Figure 16B:
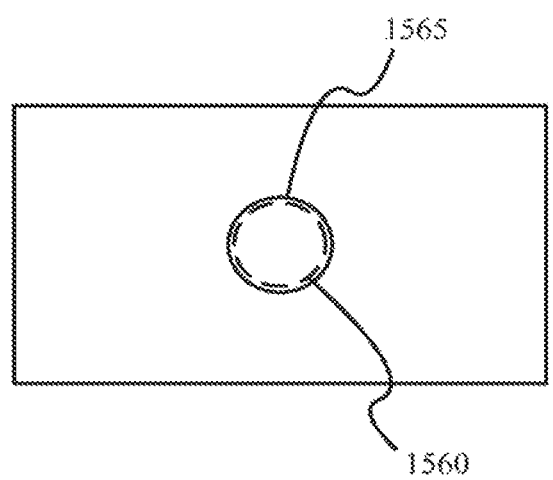
FIG. 16B shows an example of a laser spot size using the laser catheter shown in FIG. 16A.

Using the liquid light guide with a diverting tip shown in FIG. 16A provides light outside the inner lumen diameter, and produces a larger spot size 1560 as shown in FIG. 16B. The diversion of the light results in a larger laser spot size 1560 and a corresponding ablation diameter. For example, the ablation diameter and/or spot size 1560 may be almost as large, as large as, or larger than the diameter of the catheter. The larger diameter ablation may form a more substantial opening that may, for example, encourage passage of the laser catheter through an obstruction. In some embodiments, the diverting tip 1650 may be conically shaped and produces a diverging light cone that is diverted/deflected off the conically shaped tip. By way of a non-limiting example, using such a diverting tip, laser light emitted from a laser catheter having an approximate outer diameter of 1.4 mm and an approximate inner diameter of 1.14 mm may create an ablation having an approximate diameter of 1.6 mm.

In some embodiments, the diverting tip 1650 may further include a hollow interior, for example, to permit the passage of liquid and/or light from the inner lumen 1615 to pass through the diverting tip without diversion or deflection. In such embodiments, for example, the catheter 1600 may or may not include an inner light guide 1630.

Figure 17A:
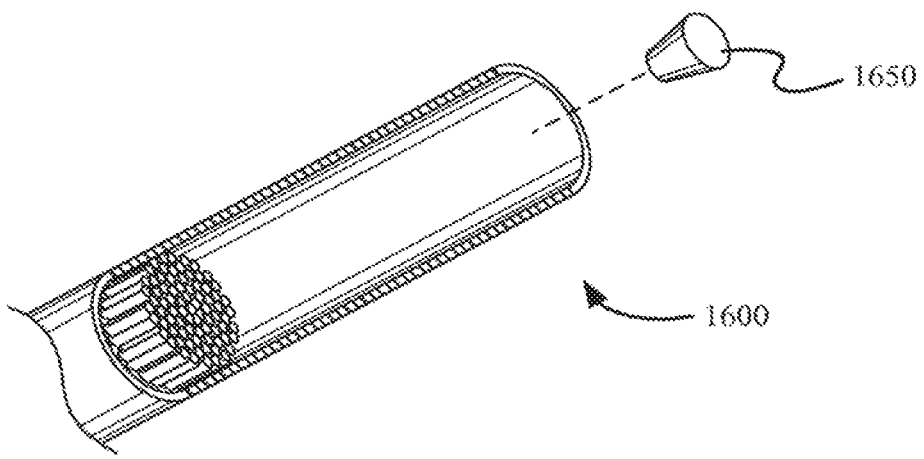
FIGS. 17A, B, and C show the distal end of a laser catheter with different shaped divesting cones according to some embodiments.
Figure 17B:
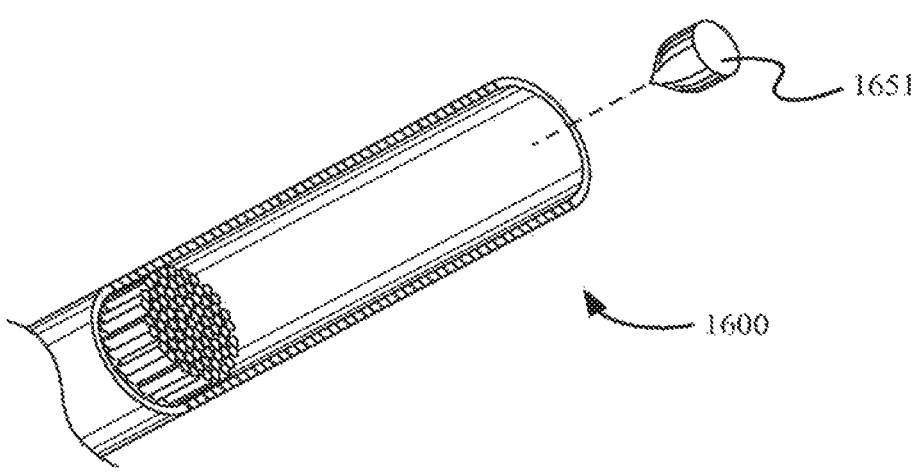
Figure 17C:
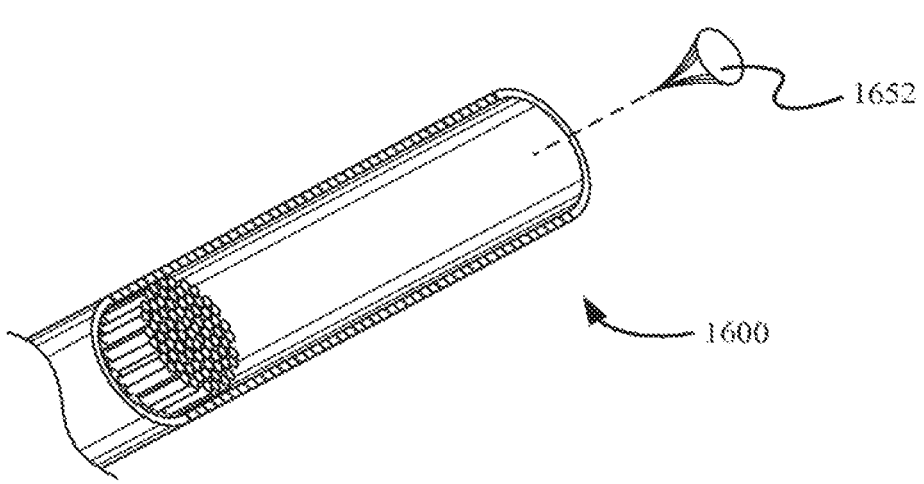

FIGS. 17A, B, and C show various examples of diverting tips 1650, 1651, and 1652 incorporated within the distal end of a laser catheter. In some embodiments, a diverting tip may include a cone with a linear taper. As shown in FIG. 17A, cone shaped diverting tip 1650 may be placed within the distal tip of liquid laser catheter 1600. FIG. 17B shows acorn shaped diverting tip 1651 with a convex taper that may be placed within the distal tip of a liquid laser catheter 1600. FIG. 16C shows funnel shaped diverting tip 1652 with a concave taper that may also be placed within the distal tip of a liquid laser catheter 1600. Diverting tips 1650, 1651, and 1652 shown in FIGS. 17A, B, and C may come in any of various other sizes and/or shapes. For example, in some embodiments, the cross section of a diverting tip may be round, oval or polygonal shaped. As shown in these figures, the taper may be linear, convex and/or concave.

Figure 18:
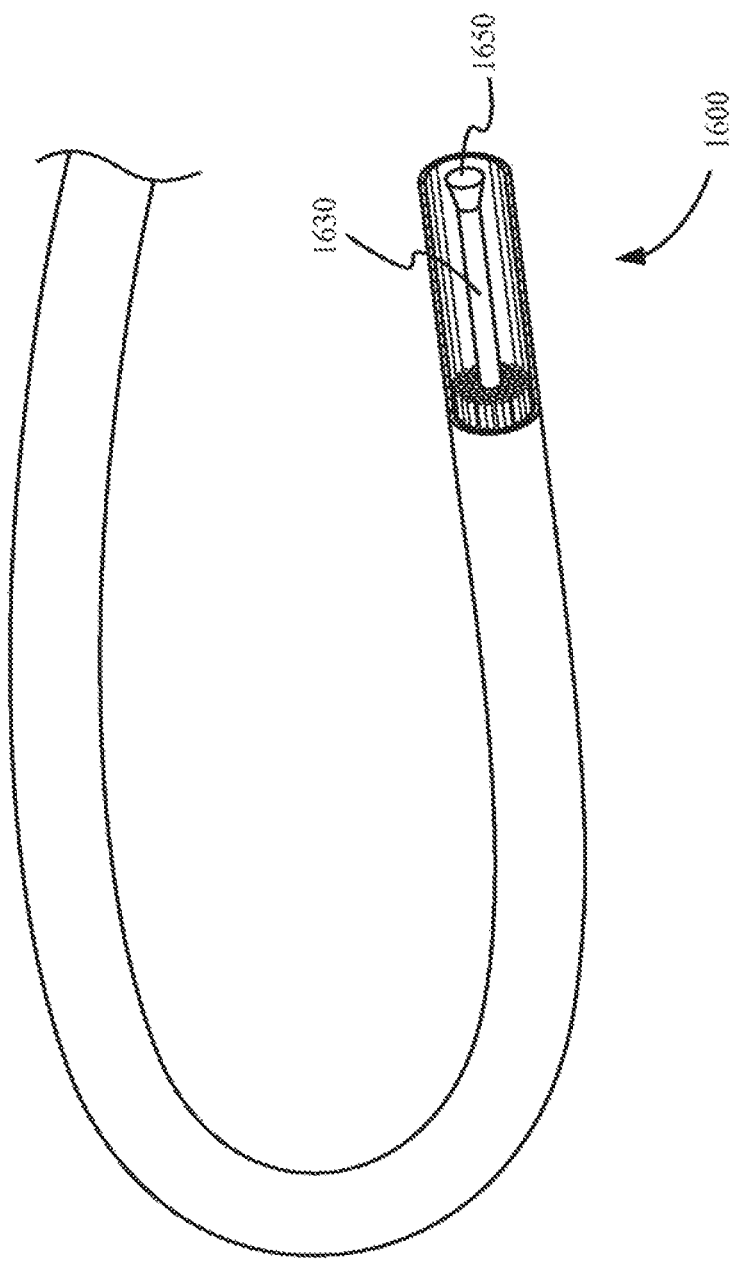
FIG. 18 shows a portion of a catheter incorporating a diverting cone according to one embodiment.

FIG. 18 shows laser catheter 1600 with a central optical fiber 1630 that includes a diverting tip 1650 coupled at the distal end according to one embodiment. The diverting tip 1650 can be coupled with central optical fiber 1630 using various methods including adhesives, mechanical holding devices, interference fit, etc. In other embodiment, diverting tip 1650 is integral with central optical fiber 1630.

Figure 19A:
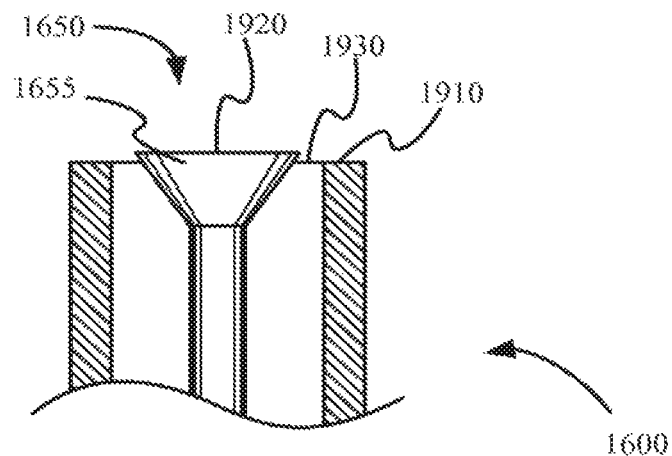
FIGS. 19A, B, and C show various examples of placement of the diverting tip within the distal end of a catheter according to some embodiments.

FIGS. 19A, B, and C show cross sections of the distal end of laser catheters 1600 with various placements of diverting tip 1655 within the distal end of laser catheter 1600, according to some embodiments. While these embodiments show diverting tips coupled with central optical fibers, however, such central optical fibers are not necessarily needed. As shown in FIG. 19A, distal end 1920 of diverting tip 1655 extends partially past distal tip 1910 of laser catheter 1600. The diameter of distal end 1920 of diverting tip 1655 may vary to allow for a greater or smaller gap 1930 between the distal tip 1655 and sheath 1610. Moreover, the position of the diverting tip 1655 may also be moved in order to change the width of gap 1930.

Figure 19B:
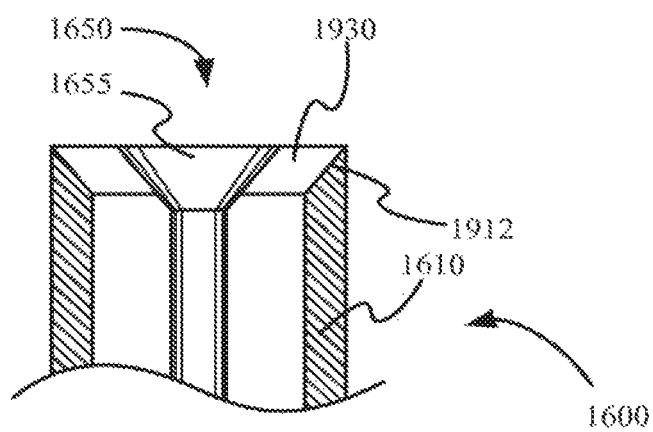
Figure 19C:
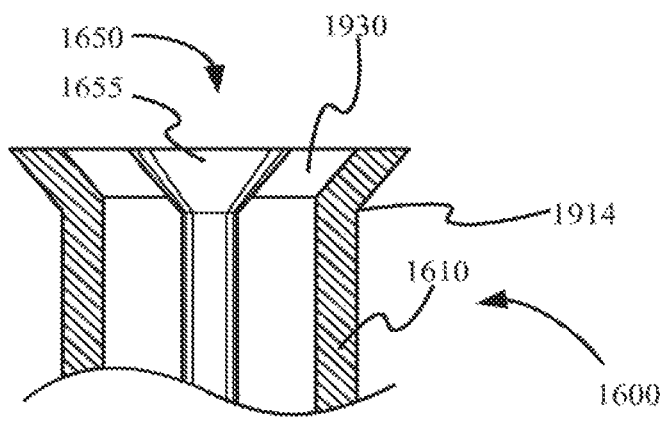

FIG. 19B shows a sheath 1610 with a chamfer 1912, according to one embodiment. Using chamfer 1912 may increase the width of gap 1930 and, therefore, provide a greater flow of liquid from catheter 1600 through gap 1930. FIG. 19C shows a sheath 1610 with bend or kink 1914. Bend or kink 1914 may increase the width of gap 1930. Increasing the width of gap 1910 may provide for increased liquid flow from catheter 1600. Such an increase in the width of gap 1930, for example, may also change the flow of liquid from the catheter 1600. Moreover, the width, shape and/or angle of gap 1930 may provide a larger or smaller resulting spot size.

Figure 20A:
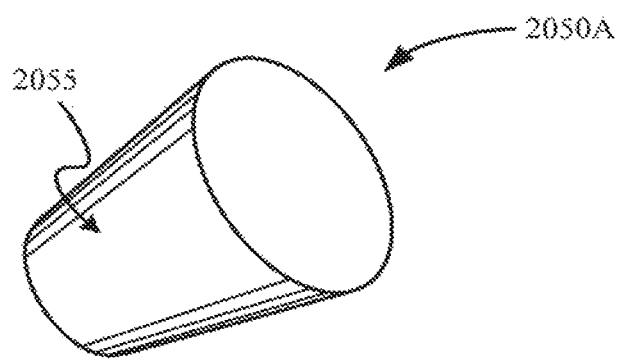
FIGS. 20A, B, C, D, and E show various diverting cone configurations according to various embodiments.
Figure 20B:
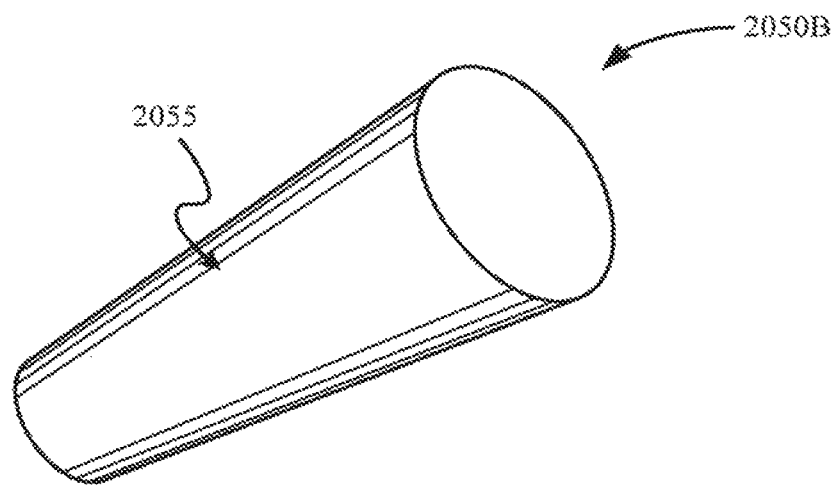
Figure 20C:
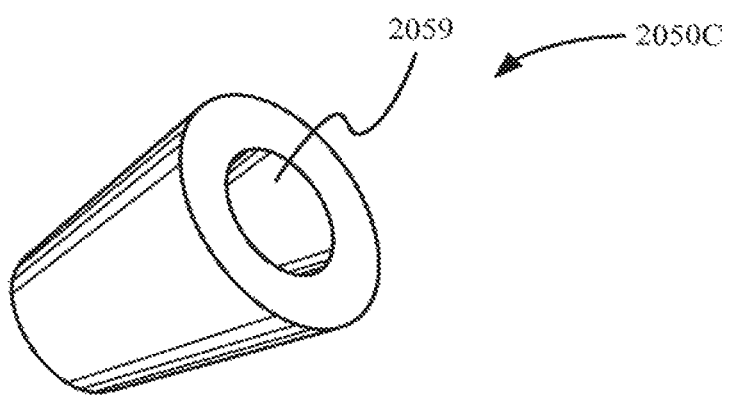
Figure 20D:
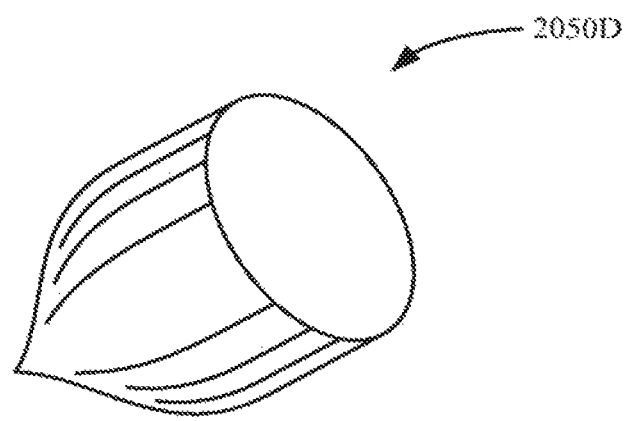
Figure 20E:
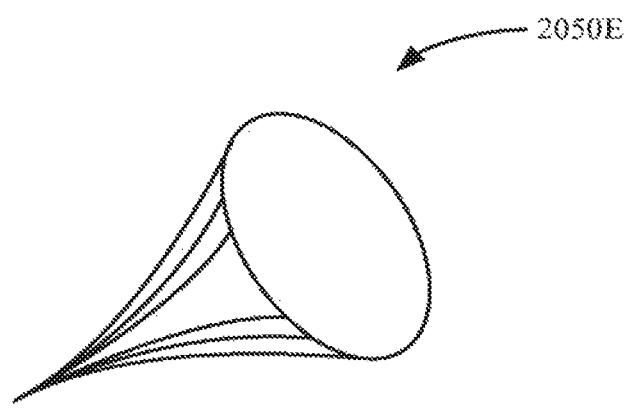

FIGS. 20A-E show various embodiments of diverting tips 2050, according to various embodiments. FIGS. 20A and 20B show solid diverting tips 2050A and 2050B. Diverting tip 2050B shown in FIG. 20B has a more gradual taper 2055 than diverting tip 2050A shown in FIG. 20A. FIG. 20C shows hollow diverting tip 2050C with aperture 2059 according to another embodiment. FIGS. 20D and 20E show convex tapered diverting tip 2050D and concave tapered diverting tip 2050E respectively according to various embodiments. Concave and/or convex diverting tips 2050D and 2050E may also be hollow and/or include a central aperture. Moreover, diverting tips 2050D and 2050E may also be hollow and/or include a central aperture. Moreover, diverting tips 2050D and 2050E may not necessarily taper to a point as shown in FIGS. 20D and 20E. While FIGS. 20A-E show solid diverting tips 2050, these diverting tips, for example, may also be hollow and/or include a channel through a central axis of the diverting tip 2050.

Figure 21A:
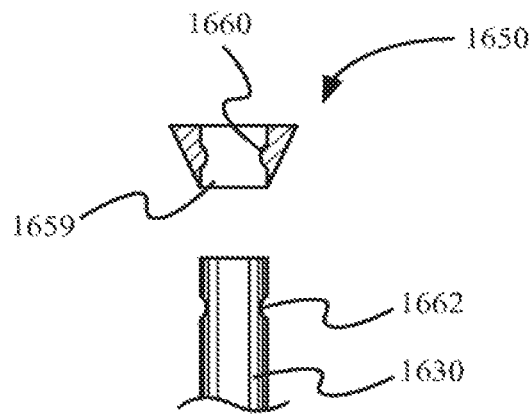
FIGS. 21A, B, and C show various attachment mechanisms for coupling a diverting cone with a fiber optic according to various embodiments.
Figure 21B:
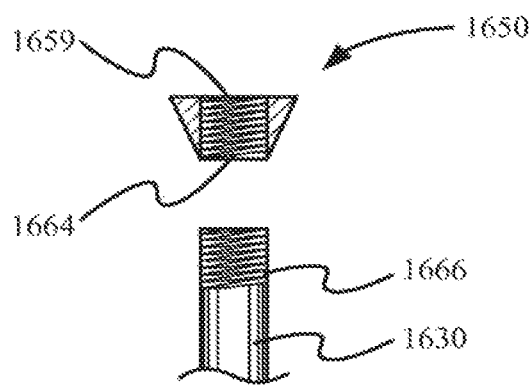
Figure 21C:
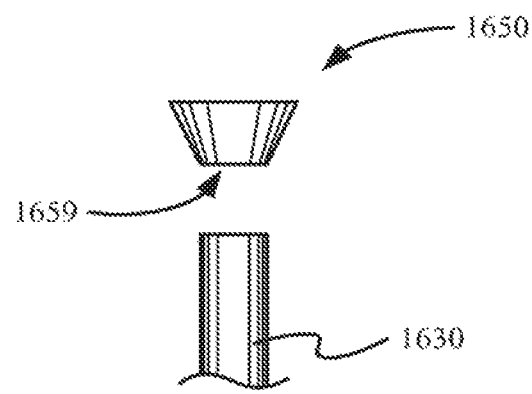

FIGS. 21A-C show various methods of attaching diverting tip 1650 to central optical fiber 1630. According to one embodiment, aperture 1659 may have a portion of its surface raised 1660 and central optical fiber 1630 may have a corresponding portion of its surface curved so that the two surfaces mate together when diverting tip 1650 is fitted with central optical fiber 1630. Likewise, aperture 1659 and central optical fiber 1630 could be fitted with corresponding threads, 1664 and 1666 respectively, so that diverting tip 1650 could be threadingly secured to central optical fiber 1630. Additionally, the inner diameter of aperture 1659 could be sized slightly smaller than the outer diameter of central optical fiber 1630 so that an interference fit is provided between aperture 1659 and central optical fiber 1630. Alternatively, diverting tip 1650 could be constructed of heat shrink material so that, upon the addition of heat, diverting tip 1650 shrinks onto the surface of central optical fiber 1630. Other methods of attaching diverting tip 1650 to central optical fiber 1630 could be employed such as using adhesives, detents, mechanical fasteners, etc.

Figure 22:
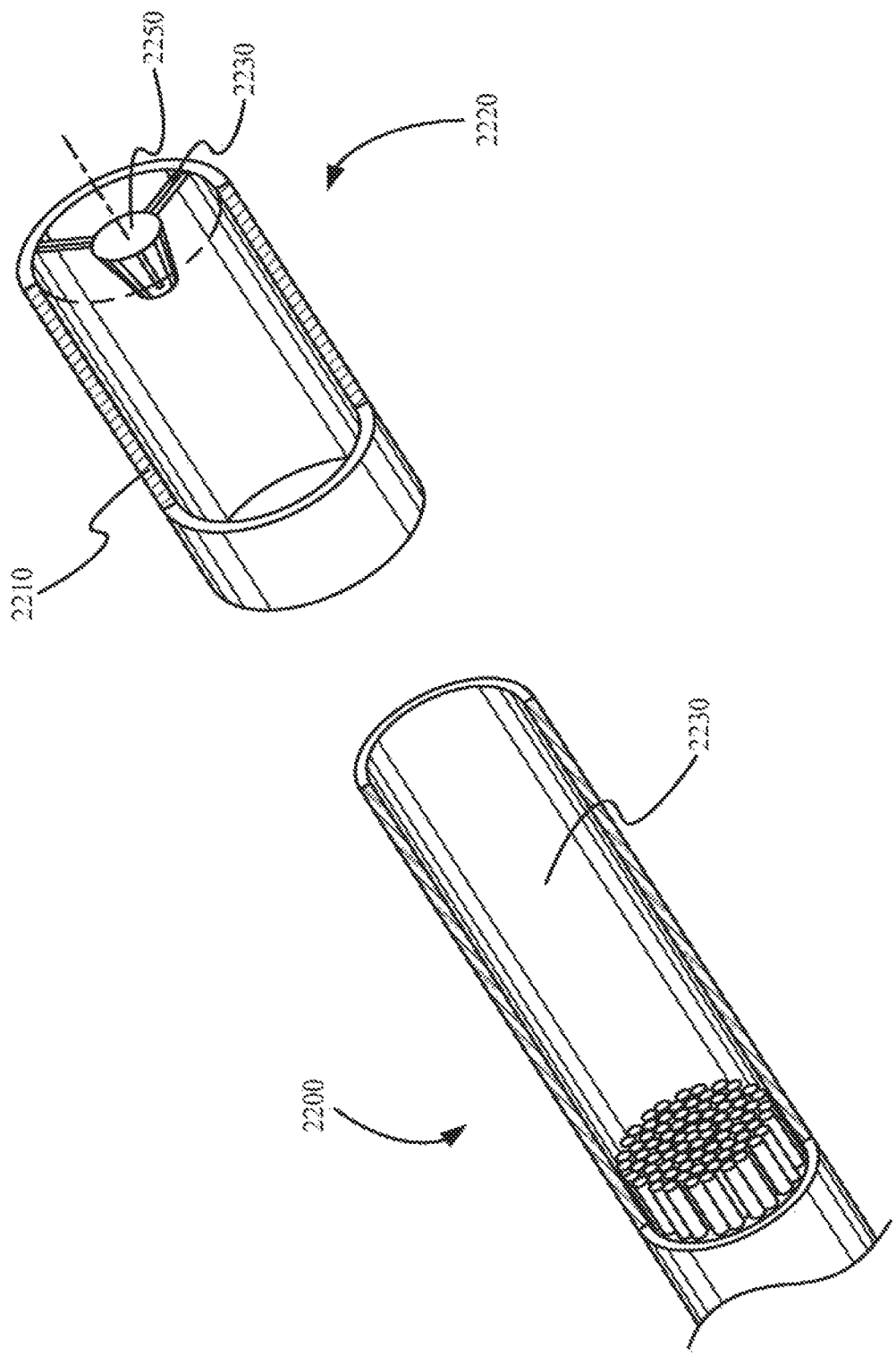
FIG. 22 shows a detachable tip apparatus with a diverting cone that can be coupled with the distal end of a laser catheter according to some embodiments.

FIG. 22 shows a diverting tip attachment 2220 coupled with a laser catheter 2200 according to another embodiment. Diverting tip attachment 2220 may be a removable distal tip that may be added or removed from the laser catheter 2200. For example, diverting tip attachment 2220 may be removably coupled with a standard laser catheter 2200. Thus, in use, for example, a physician may add a diverting tip attachment 2220 to a standard laser catheter in order to increase the spot size of the catheter. Diverting tip attachment 2220 includes a housing 2210 with a diverting tip 2250 coupled within. Diverting tip 2250 may be secured within diverting tip attachment 2220 using one or more attachment members 2230. For example, attachment members 2230 may include string, wire or other material that couples diverting tip 2250 with diverting tip attachment 2200 and provide liquid flow therebetween. Diverting tip 2250 shown in FIG. 22, in some embodiments may have a channel through the central axis of the diverting tip 2250. In yet other embodiments, diverting tip 2250 may be hollow.

Figure 23A:
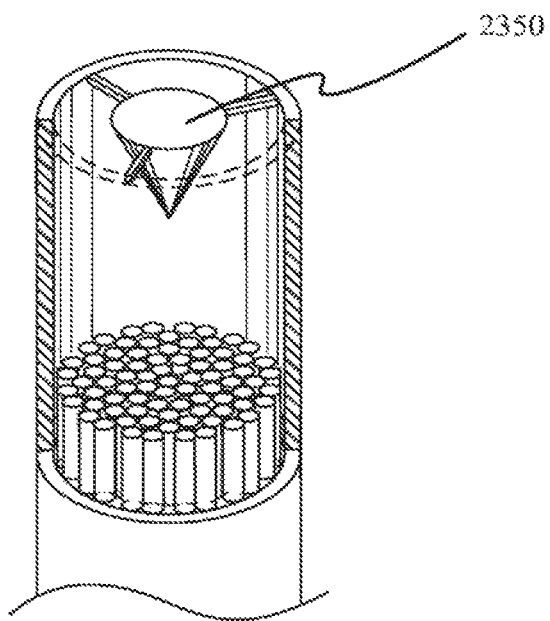
FIGS. 23A and B show attachment mechanisms for a diverting cone within a laser catheter according to one embodiment.
Figure 23B:
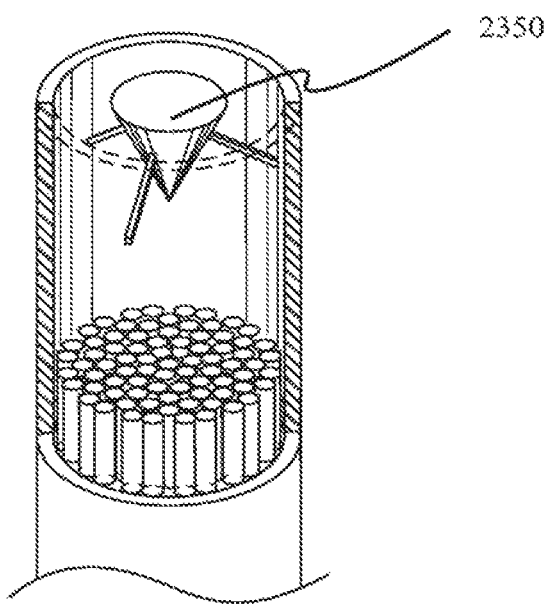

FIGS. 23A and B show two different attachment mechanisms for diverting tip 2350 within a laser catheter and/or within a diverting tip attachment according to some embodiments. As shown in the figures, the diverting tip 2350 may be secured at the distal end of diverting tip 2350 or along the tapered portion of diverting tip 2350 according to various embodiments. Various other attachment schemes may be employed. In some embodiments, diverting tip 2350 may be secured using various wires and/or strings. In other embodiments, diverting tip 2350 may be secured in such a way to allow liquid to flow between the outer sheath and the diverting tip 2350. In some embodiments, for example, diverting tips 2350 may be hollow and/or include a channel through the central axis of the diverting tip 2350.

Specific details are given in the above description to provide a thorough understanding of the embodiments. However, it is understood, that the embodiments may be practiced without these specific details. For example, circuits, structures, and/or components may be shown in block diagrams in order not to obscure the embodiments in unnecessary detail. In other instances, well-known circuits, processes, algorithms, structures, components, and techniques may be shown without unnecessary detail in order to avoid obscuring the embodiments.

While the principles of the disclosure have been described above in connection with specific apparatuses and methods this description is made only by way of example and not as limitation on the scope of the disclosure.

What is claimed is:

1. A catheter comprising:
   a sheath having a distal end, a liquid infusion port, and an inner lumen extending from the liquid infusion port to the distal end of the sheath, wherein the inner lumen is configured to receive fluid introduced into the liquid infusion port, wherein the inner lumen has a distal portion;
   a diverting tip positioned within the inner lumen, the diverting tip having a proximal end and a distal end, wherein the distal end of the diverting tip is larger than the proximal end of the diverting tip and is configured to divert at least a portion of fluid, wherein the distal end of the diverting tip is smaller than the distal portion of the inner lumen; and
   a plurality of optical fibers having a distal end disposed within the inner lumen proximal to the diverting tip and configured to transmit light within the inner lumen.

2. The catheter of claim 1, wherein the diverting tip is hollow.

3. The catheter of claim 1, wherein the sheath comprises a tubular structure that surrounds the inner lumen, wherein the tubular structure is constructed from a material configured to induce reflection of light within the fluid.

4. The catheter of claim 1, wherein the diverting tip is constructed from a material configured to induce internal reflection of light within the fluid.

5. The catheter of claim 1, wherein the diverting tip is further capable of permitting a portion of the light to exit the catheter tip without diverting the light.

6. The catheter of claim 1, wherein the deflecting member is conical in shape.

7. The catheter of claim 1, wherein the diverting tip creates a gap between the diverting tip and the sheath.

8. The catheter of claim 7, wherein the gap is adjustable.

9. The catheter of claim 7, wherein the diverting tip creates a proximal gap between the proximal end of the diverting tip and the sheath and a distal gap between the distal end of the diverting tip and the sheath.

10. The catheter of claim 9, wherein the proximal gap is greater than the distal gap.

11. The catheter of claim 1, wherein the diverting tip is removably coupled to the sheath.

\* \* \* \* \*